(12) United States Patent
Mechoulam et al.

(10) Patent No.: US 9,365,534 B2
(45) Date of Patent: Jun. 14, 2016

(54) ARYLATED CAMPHENES, PROCESSES FOR THEIR PREPARATION AND USES THEREOF

(71) Applicant: Yissum Research Development Company of the Hebrew University of Jerusalem Ltd., Jerusalem (IL)

(72) Inventors: Raphael Mechoulam, Jerusalem (IL); Lital Magid, Jerusalem (IL); Esther Shohami, Mevasseret Zion (IL); Itai Bab, Carmei Yossef (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 0 days.

(21) Appl. No.: 14/230,267

(22) Filed: Mar. 31, 2014

(65) Prior Publication Data

US 2015/0038728 A1 Feb. 5, 2015

Related U.S. Application Data

(62) Division of application No. 13/504,167, filed as application No. PCT/IL2010/000970 on Nov. 18, 2010, now Pat. No. 8,722,938.

(60) Provisional application No. 61/262,677, filed on Nov. 19, 2009.

(51) Int. Cl.
| | |
|---|---|
| *C07D 493/00* | (2006.01) |
| *C07D 311/94* | (2006.01) |
| *C07C 39/23* | (2006.01) |
| *C07C 43/215* | (2006.01) |
| *C07C 43/23* | (2006.01) |
| *C07C 45/70* | (2006.01) |
| *C07C 51/00* | (2006.01) |
| *C07C 51/09* | (2006.01) |
| *C07C 69/757* | (2006.01) |
| *C07D 311/80* | (2006.01) |
| *C07D 311/96* | (2006.01) |

(52) U.S. Cl.
CPC .............. *C07D 311/94* (2013.01); *C07C 39/23* (2013.01); *C07C 43/215* (2013.01); *C07C 43/23* (2013.01); *C07C 45/70* (2013.01); *C07C 51/00* (2013.01); *C07C 51/09* (2013.01); *C07C 69/757* (2013.01); *C07D 311/80* (2013.01); *C07D 311/96* (2013.01); *C07C 2102/42* (2013.01)

(58) Field of Classification Search
CPC ..................................................... C07C 43/215
USPC ....................................................... 546/279
See application file for complete search history.

(56) References Cited

U.S. PATENT DOCUMENTS

| | | | |
|---|---|---|---|
| 2,537,647 A | 1/1951 | Kitchen et al. | |
| 2,647,152 A | 7/1953 | Kitchen et al. | |
| 3,284,359 A | 11/1966 | Roth | |
| 3,800,051 A | 3/1974 | Barnhart et al. | |
| 3,833,671 A | 9/1974 | Mardiguian et al. | |
| 4,061,777 A | 12/1977 | Mardiguian | |
| 4,112,000 A | 9/1978 | Mardiguian | |
| 5,648,352 A | 7/1997 | Bock et al. | |
| 6,242,386 B1 | 6/2001 | Lukads et al. | |
| 7,514,583 B2 | 4/2009 | Snow et al. | |
| 7,714,170 B2 | 5/2010 | Snow et al. | |
| 8,722,938 B2 * | 5/2014 | Mechoulam et al. | 568/327 |
| 2007/0225362 A1 | 9/2007 | Snow et al. | |
| 2007/0276034 A1 | 11/2007 | Esposito et al. | |
| 2011/0015272 A1 | 1/2011 | Snow et al. | |
| 2011/0144124 A1 | 6/2011 | Snow et al. | |

FOREIGN PATENT DOCUMENTS

| | | |
|---|---|---|
| CL | 199300256 | 2/1993 |
| CL | 200001176 | 5/2000 |
| CN | 1847207 A | 3/2006 |
| DE | 828394 C | 1/1952 |
| DE | 876241 C | 5/1953 |
| GB | 1548875 A | 7/1979 |
| JP | S50151856 A | 12/1975 |
| JP | 2004513163 A | 4/2004 |
| JP | 2004529852 A | 9/2004 |
| JP | 2005531596 A | 10/2005 |
| RU | 2233262 C1 | 7/2004 |
| WO | 0224636 A2 | 3/2002 |
| WO | 0238542 A1 | 5/2002 |
| WO | 03101927 A1 | 12/2003 |
| WO | WO 2008/154083 A2 | 12/2008 |

OTHER PUBLICATIONS

Murry et al. Tetrahedron Letters, 24(10), 979-982, 1983.*
Tsukervanik, et al. STN Abstract of Zhurnal Obshchei Khimii (1938), 8, 1899-1902.*
Kitchen, Leland J. Journal of the American Chemical Society (1948), 70, 3608-10.*
Herold et al. Chemische Berichte (1981), 114(1), 359-74.*
Duclos et al Tetrahedron Letters, 2008, 49, 5587-5589.*
Makriyannis A, "Bornyl- and Isobornyl-delta8-tetrahydrocannabinols: A Novel Class of Cannabinergic Ligands," J. of Medicinal Chemistry, Oct. 2008, pp. 6393-6399, vol. 51.
Duclos Ri, et al, "Synthesis and Characterization of 2-substituted Bornane Pharmacophores for Novel Cannabinergic Ligands", Tetrahedron Letters, Sep. 2008, pp. 5587-5589, vol. 49, No. 39, Elsevier, Amsterdam, NL.
Szabo, B. "Pharmacology of cannabinoid receptors." Biotrend Rev 2 (2008): 1-13.

(Continued)

*Primary Examiner* — Nizal Chandrakumar
(74) *Attorney, Agent, or Firm* — Browdy and Neimark, PLLC

(57) ABSTRACT

The present invention relates to arylated camphenes, processes for their preparation and uses thereof for the manufacture of medicaments for the treatment of diseases, disorders or conditions associated with, or benefiting from stimulation of CB2 receptors.

4 Claims, 10 Drawing Sheets

(56) References Cited

OTHER PUBLICATIONS

Harry E. Albert J of Am. Chem. Society 76:4985-4988 (Oct. 1954).
Moldovanskaya et al "Products of Condensation of Camphene with 2,5-,3,4-, and 3,5-xylenols", Trudy Vsesoyuznogo 7:46-51 (1965).
Richard I. Duclos Jr. et al, "Synthesis and characterization of 2-substituted bornane pharmacophores for novel cannabinergic ligands" Tetrahedron Letters, 49:5587-5589 (2008).
T. Herold et al, "Asymmetrische Synthesen von 4-Penten-2-ol uber Allylboronsaureester chiraler Glycole" Chemische Berichte. 114:1:359-374 (1981).
Albrecht Berkessel et al, "Synthesis and Configurational Assignment of Chiral Salicylic Aldehydes: Novel Building Blocks for Asymmetric Catalysis" Europ. J of Organic Chemistry. 16:2800-2807 (2002).
Arevalo-Martin A, Garcia-Ovejero D, Gomez O, Rubio-Araiz A, Navarro-Galve B, Guaza C, Molina-Holgado E, Molina-Holgado F, "CB2 Cannabinoid Receptors as an Emerging Target for Demyelinating Diseases: From Neuroimmune Interactions to Cell Replacement Strategies", British J. Pharmacology., Jan. 2008, pp. 216-225, vol. 153, No. 2.
Avraham Y, Israeli E, Gabbay E, Okun A, Zolotarev O, Silberman I, Ganzburg V, Dagon Y, Magen I, Vorobia L, Pappo O, Mechoulam R, Ilan Y, Berry EM, "Endocannabinoids Affect Neurological and Cognitive Function in Thioacetamide-Induced Hepatic Encephalopathy", Neurobiological Disease, Jan. 2006, pp. 237-245, vol. 21, No. 1.
Ashton JC, Glass M, "The Cannabinoid CB2 Receptor as a Target for Inflammation-Dependent Neurodegeneration", Current Neuropharmacology, Jun. 2007, pp. 73-80, vol. 5, No. 2.
Ashton JC, Rahman RM, Nair SM, Sutherland BA, Glass M, Appleton I, "Cerebral Hypoxia-Ischemia and Middle Cerebral Artery Occlusion Induce Expression of the Cannabinoid CB2 Receptor in the Brain", Neuroscience Letters, Jan. 2007, pp. 114-117, vol. 412, No. 2.
Bartlett PD, Knox LH, Org. Syn. Coll., 1973, p. 689, vol. 5.
Benito C, Tolon RM, Pazos MR, Nunez E, Castillo AL, Romero J, "Cannabinoid CB2 Receptors in Human Brain Inflammation", British J. Pharmacology, Jan. 2008, pp. 277-285, vol. 153, No. 2.
Bilsland LG, Dick Jr, Pryce G, Petrosino S, Dimarzo V, Baker D, Greensmith L., "Increasing Cannabinoid Levels by Pharmacological and Genetic Manipulation Delay Disease Progression in SOD1 Mice", FASEB J., May 2006, pp. 1003-1005, vol. 20, No. 7.
Centonze D, Rossi S, Finazzi-Agro A, Bernardi G, Maccarrone M, "The (Endo)canabinoid System in Multiple Sclerosis and Amyotrophic Lateral Sclerosis", International Review of Neurobiology, 2007, pp. 171-186, vol. 82.
Chen Y, Constantini S, Trembovler V, Weinstock M, Shohami E., "An Experimental Model of Closed Head Injury in Mice: Pathophysiology, Histopathology, and Cognitive Deficits", J. Neurotrauma, Oct. 1996, pp. 557-568, vol. 13.
Dagon Y, Avraham Y, Ilan Y, Mechoulam R, Berry EM, "Cannabinoids Ameliorate Cerebral Dysfunction Following Liver Failure Via AMP-Activated Protein Kinase", FASEB J., Aug. 2007, pp. 2431-2441, vol. 21.
Docagne F, Mestre L, Loria F. Hernangomez M, Correa F, Guaza C, "Therapeutic Potential of CB2 Targeting in Multiple Sclerosis", Expert Opinion on Therapeutic Targets, Feb. 2008, pp. 185-195, vol. 12., No. 2.
Dominianni SJ, Ryan CW, Dearmitt CW, "Synthesis of 5-(Tert-alkyl) Resorcinols", J. Org. Chem., Jan. 1977, pp. 344-346, vol. 42.
Fernandex-Ruiz J, Gonzales S, Romero J, Ramos JA, "Cannabinoids in Neurodegeneration and Neuroprotection", Cannabinoids as Therapeutics, 2005, pp. 79-109, Mechoulam R. (ed.), Birkhauser Verlag, Basel, Switzerland.
Fernandez-Ruiz J, Pazos MR, Garcia-Arencibia M, Sagredo O, Ramos JA, "Role of CB2 Receptors in Neuroprotective Effects of Cannabinoids", Mol. Cell. Endocrin., Apr. 2008, pp. S91-S96, vol. 286, Supp. 1.
Hanus L, Breuer A, Tchilibon S, Shiloah S, Goldenberg DM, Horowitz M, Pertwee RG, Ross RA, Mechoulam R, Fride E., "HU-308: A Specific Agonist for CB2, a Peripheral Cannabinoid Receptor", Proceedings of the National Academy of Sciences (USA), Dec. 1999, 14228-14233, vol. 96.
Hanus LO, Tchilibon S, Ponde DE, Breuer A, Fride E, Mechoulam R, "Enantiomeric Cannabidiol Derivatives: Synthesis and Binding to Cannabinoid Receptors", Org. Biomolecular Chemistry, Feb. 2005, pp. 1116-1123, vol. 3, No. 6.
Hertzog DL, "Recent Advances in the Cannabinoids" Expert Opinion on Therapeutic Patents, Oct. 2004, pp. 1435-1452, vol. 14, No. 10.
Klegeris A, Bissonnete CJ, McGeer PL, "Reduction of Human Monocytic Cell Neurotoxicity and Cytokine Secretion by Ligands of the Cannabinoid-type CB2 Receptor", British J. Pharmacology, Jun. 2003, pp. 775-786, vol. 139, No. 4.
Kogan NM, Mechoulam R, "The Chemistry of Endocannabinoids", J. Endocrinological Investigation, 2006, pp. 3-14, vol. 29, Supp. 3.
Kogan NM, Mechoulam R, "Cannabinoids in Health and Disease", Dialogues in Clinical Neuroscience, 2007, pp. 413-430, vol. 9, No. 4.
Lotersztajn S, Teixeira-Clerc F, Julien B, Deveaux V, Ichigotani Y, Manin S, Tran-Van-Nhieu J, Karsak M, Zimmer A, Mallat A, "CB2 Receptors as New Therapeutic Targets for Liver Diseases", British J. Pharmacology, Jan. 2008, pp. 286-289, vol. 153, No. 2.
McMurray JE, Scott WJ, "A Method for the Regiospecific Synthesis of Enol Triflates by Enolate Trapping", Tetrahedron Letters, 1983, pp. 979-982, vol. 24, No. 10.
Mechoulam R, Braun P, Gaoni Y, "Synthesis of (Delta)1-THC and Related Cannabinoids", J. Am. Chem. Soc., 1972, pp. 6159-6165, vol. 94.
Mechoulam R, Sumariwalla PF, Feldmann M, Galilly R, "Cannabinoids in Models of Chronic Inflammatory Conditions", Phytochemistry Reviews, 2005, pp. 11-18, vol. 4.
Ofek O, Karsak, M, Leclerc N, Fogel M, Frenkel B, Wright K, Tam J, Attar-Namdar M, Kram V, Shohami E, Mechoulam R, Zimmer A, Bab I, "Peripheral Cannabinoid Receptor, CB2, Regulates Bone Mass", Proceedings of the National Academy of Sciences (USA), Jan. 2006, pp. 696-701, vol. 103, No. 3.
Pacher P, Hasko G, Endocannabinoids and Cannabinoid Receptors in Ischaemia-Reperfusion Injury and Preconditioning, British J. Pharmacology, Jan. 2008, pp. 252-262, vol. 153.
Palazuelos J, Aguado T, Egia A, Mechoulam R, Guzman M, Galve-Roperh I, "Non-psychoactive CB2 Cannabinoid Agonists Stimulate Neural Progenitor Proliferation", FASEB J., Nov. 2006, pp. 4337-4345, vol. 580.
Palazuelos J, Davoust N, Julien B, Hatterer E, Aguado T, Mechoulam R, Benito C, Romero J, Silva A, Guzman M, Nataf S, Galve-Roperh I, "The CB2 Cannabinoid Receptor Controls Myeloid Progenitor Trafficking: Involvement in the Pathogenesis of an Animal Model of Multiple Sclerosis", J. Biol. Chem., May 2008, 13320-13329, vol. 283.
Steffens S, Mach F, "Cannabinoid Receptors in Atherosclerosis", Current Opinion in Lipidology, Oct. 2006, pp. 519-526, vol. 17, No. 5.
Steffens S, Veillard NR, Arnaud C, Pelli G, Burger F, Staub C, Karsak M, Zimmer A, Frossard JL, Mach F, "Low Dose Oral Cannabinoid Therapy Reduces Progression of Atherosclerosis in Mice", Nature, Apr. 2005, pp. 782-786, vol. 434, No. 7034.
Thoren S, "4 Isomeric Alpha-Hydroxybornanones", Acta Chemica Scandinavica, 1970, pp. 93-98, vol. 24.
Van Sickle MD, Duncan M, Kingsley PJ, Mouihate A, Urbani P, Mackie K, Stella N, Makriyannis A, Piomelli D, Davison JS, Marnett LI, Di Marzo V, Pittman QJ, Patel KD, Sharkey KA, Identification and Functional Characterization of Brainstem Cannabinoid CB2 Receptors, Science, Oct. 2005, pp. 329-332, vol. 310, No. 5746.
Yamamoto W, Mikami T, Iwamura H, "Involvement of Central Cannabinoid CB2 Receptor in Reducing Mechanical Allodynia in a Mouse Model of Neuropathic Pain", European J. Pharmacology, Mar. 2008, pp. 56-61, vol. 583, No. 1.
Zhang M, Martin BR, Adler MW, Razdan RK, Ganea D, Tuma RF, "Modulation of the Balance Between Cannabinoid CB1 and CB2 Receptor Activation During Cerebral Ischemic/Reperfusion Injury", Neuroscience, Mar. 2008, pp. 753-760, vol. 152, No. 3.
Pertwee RG, Gibson TM, Stevenson LA, Ross RA, Banner WK, Saha B, Razdan RK, Martine BR, "O-1057, a Potent Water-Soluble Can-

(56) References Cited

OTHER PUBLICATIONS nabinoid Receptor Agonist with Antinociceptive Properties," British J. Pharmacology, Apr. 2000, pp. 1577-1584, vol. 129, No. 8.
Shohami E, Gallily R, Mechoulam R, Bass R, Ben-Hur T, "Cytokine Production in the Brain Following Closed Head Injury: Dexanabinol (HU-211) is a Novel TNF-alpha Inhibitor and an Effective Neuroprotectant", J. Neuroimmunology, Feb. 1997, pp. 169-177, vol. 72, No. 2.
Ross RA, Brockie HC, Stevenson LA, Murphy VL, Templeton F, Makriyannis A, Pertwee RG, Agonist-Inverse Agonist Characterization at CB1 and CB2 Cannabinoid Receptors of L759633, I759656 and AM630, British J. Pharamcology, Feb. 1999, pp. 665-672, vol. 126, No. 3.
Beni-Adani L, Gozes I, Cohen Y, Assaf Y, Steingart RA, Brenneman DE, Eizenberg O, Trembolver V, Shohami E, A Peptide Derived from Activity-Dependent Neuroprotective Protein (ADNP) Ameliorates Injury Response in Closed Head Injury in Mice, J. Pharmacology and Experimental Therapeutics, Jan. 2001, pp. 57-63, vol. 296, No. 1.
Dorwald "Oraganic Synthesis: General Remarks" Wiley-VCH 1.2: 1-16 (2005).
Duclos Jr. Richard, et al "Synthesis and characterization of 2-substituted bornane pharmacophores for novel cannabinergic ligands" Tetrahedron Letters 49:39: 5587-5589 (Jul. 2008).
Lu, Dai et al "Bornyl- and Isobornyl-8-tetrahydrocannabinols: A Novel Class of Cannabinergic Ligands" J. Med. Chem. 51:6393-6399 (Oct. 2008).
I. Yu et al Alkylation of Pyrocatechol and Resorcinal by Camphene: Chemistry of Natural Compounds 43:3: 245-249 (May-Jun. 2007).
T.A Rudolfi "Determining Positions of Substituents in Disubstituted Phenols From Infrared Spectra" Zhurnal Prikladnoi Spektroskopii 7:5:698-703 (1967).
V.V. Fomenko et al "Alkylation of Phenol and its Derivatives with Camphene on Large-Porpus B-Zeolite" Russian Journal of Organic Chemistry 36:4 564-576(2000).
I. Oleinik et al "Design of Schiff Base-Like Postmetallocene Catalytic Systems for Polymeriation of Olefins: IX Synthesis of Salicylaldehydes Containing an Isobornyl Substituent and Hydroxyphenyl Imine Ligands based thereon" Russian Journal of Organic Chemistry 44:1: 107-113 (2008).
Wu, Bi-Qi et al "Stereochemistry of the coupling step in photo-Sml reaction" Chinese journal of chemistry 10:3: (1992).
L. M . Shulov et al "Products of the Alkylation of m-Cresol with Camphene" Terpenophenols 5:1: 77-82 (Jan. 1969).
Ernst T. Theimer et al "Olfaction and Molecular Shape. Chirality as a Requisite for Odor" Journal of Agricultural and Food Chemistry. 25:5: 1168-1177 11(May 1977).
C.R.Hughes et al "Silica and Alumina Catalysed reactions of some monoterpene derivatives" Tetrahedron. T27: 2247-2253 (Mar. 1971).
D.E. Bays et al"Absorption Spectra of Ketones. Part IX. Ultraviolet Spectra and Circular Dichroism of Bornenones and Other By-Unsturated Ketones" Phys. Org. B: 215-226 (1967).
William F. Erman et al "Stereospecific Synthesis of p-Bornyl- and p-Isobornylphenol" Journal of American Chemical society. 27:1526-1535 (May 1962).
William F. Erman "The condensation of Camphene and Phenol. Product Formation via a Direct 2,6-Hydride Transfer1" Journal of the American Chemical Society. 86: 2887-2897(Jul. 1964).
Albert H. E. "Notes" Journal of American chemical Society 76: 4985-4988 (Oct. 1954).
Dirk P. Dygutsch "Ring Enlargment of Dichloromethylcyclohexadienones via Polystyrene-Supported Organotin Hydride" Synlett 363-365 (May 1994).
V.V. Fomenko et al "Reaction of Alcohols with Camphene over B-Zeolite" Russian Journal of Organic Chemistry. 33:7: 1006-1017 (1997).
Demoloe .E Helvetica Chimica Acta 47:7: 1766-1774 (1964).
Kheifits, L. A. et al Zhurnal Vsesoyuznogo himicheskogo Obshchestva im. 234-235(1962).
Liu, B.T. et al "Youjo Huaxue" 318-322(1995).
Zhurnal Organicheskoi Khimii 2059-2064 (1996).
Office Action, dated Nov. 7, 2014. In corresponding JP patent appln No. 2012-539469.

* cited by examiner

ARYLATED CAMPHENES, PROCESSES FOR THEIR PREPARATION AND USES THEREOF

FIELD OF THE INVENTION

This invention relates to arylated camphenes, processes for their preparation and uses thereof for the manufacture of medicaments for the treatment of diseases, disorders or conditions associated with, or benefiting from stimulation of CB2 receptors.

BACKGROUND OF THE INVENTION

The following publications are relevant for describing the state of the art in the field of the invention:
1. Arévalo-Martín A, García-Ovejero D, Gómez O, Rubio-Araiz A, Navarro-Galve B, Guaza C, Molina-Holgado E, Molina-Holgado F. CB2 cannabinoid receptors as an emerging target for demyelinating diseases: from neuroimmune interactions to cell replacement strategies. Br J Pharmacol. 153, 216-25 (2008).
2. Avraham Y, Israeli E, Gabbay E, Okun A, Zolotarev O, Silberman I, Ganzburg V, Dagon Y, Magen I, Vorobia L, Pappo O, Mechoulam R, Ilan Y, Berry E M. Endocannabinoids affect neurological and cognitive function in thioacetamide-induced hepatic encephalopathy. Neurobiol. Disease, 21, 237-245 (2006).
3. Ashton J C, Glass M. The cannabinoid CB2 receptor as a target for inflammation-dependent neurodegeneration. Current Neuropharmacol. 5, 73-80 (2007).
4. Ashton J C, Rahman R M, Nair S M, Sutherland B A, Glass M, Appleton I. Cerebral hypoxia-ischemia and middle cerebral artery occlusion induce expression of the cannabinoid CB2 receptor in the brain. Neurosci Lett. 412, 114-7 (2007).
5. Bartlett, P D, Knox, L H. Org. Synth. Coll. Vol. 5, 689 (1973).
6. Benito C, Tolón R M, Pazos M R, Núñez E, Castillo A I, Romero J. Cannabinoid CB2 receptors in human brain inflammation. Brit. J. Pharmacol. 153, 277-285 (2008).
7. Bilsland L G, Dick J R, Pryce G, Petrosino S, Di Marzo V, Baker D, Greensmith L. Increasing cannabinoid levels by pharmacological and genetic manipulation delay disease progression in SOD1 mice. FASEB J. 20, 1003-5 (2006).
8. Centonze D, Rossi S, Finazzi-Agrò A, Bernardi G, Maccarrone M. The (endo)cannabinoid system in multiple sclerosis and amyotrophic lateral sclerosis. Int Rev Neurobiol. 82, 171-86 (2007).
9. Chen Y, Constantini S, Trembovler V, Weinstock M and Shohami E. An experimental model of closed head injury in mice: pathophysiology, histopathology, and cognitive deficits, J. Neurotrauma 13, 557-568 (1996).
10. Dagon Y, Avraham Y, Ilan Y, Mechoulam R, Berry E M. Cannabinoids ameliorate cerebral disfunction following liver failure via AMP-activated protein kinase. FASEB J. 21, 2431-2441 (2007).
11. Docagne F, Mestre L, Loría F, Hernangómez M, Correa F, Guaza C. Therapeutic potential of CB2 targeting in multiple sclerosis. Expert Opin Ther Targets. 12, 185-95 (2008).
12. Dominianni S J, Ryan, C W, DeArmitt C W. Synthesis of 5-(tert-alkyl)resorcinols. J. Org. Chem. 42, 344-346 (1977).
13. Fernandez-Ruiz J, Gonzalez S, Romero J, Ramos J A, Cannabinoids in neurodegeneration and neuroprotection. In R. Mechoulam (Ed.) "Cannabinoids as Therapeutics". Birkhauser, Basel, 2005, pp 79-109.
14. Fernández-Ruiz J, Pazos M R, García-Arencibia M, Sagredo O, Ramos J A. Role of CB2 receptors in neuroprotective effects of cannabinoids, Mol Cell. Endocrin. 286 (Suppl 1), S91-S96 (2008).
15. Hanus L, Breuer A, Tchilibon S, Shiloah S, Goldenberg D M, Horowitz M, Pertwee R G, Ross R A, Mechoulam R, Fride E. HU-308: A specific agonist for CB2, a peripheral cannabinoid receptor. Proc. Natl. Acad. Sci. (US), 96, 14228-14233 (1999).
16. Hanus L O, Tchilibon S, Ponde D E, Breuer A, Fride E, Mechoulam R. Enantiomeric cannabidiol derivatives: Synthesis and binding to cannabinoid receptors. Org. Biomol. Chem. 3, 1116-1123 (2005).
17. Hertzog D L. Recent advances in the cannabinoids. Expert Opin. Ther. Patents, 14, 1435-1452 (2004).
18. Klegeris A, Bissonnette C J, McGeer P L. Reduction of human monocytic cell neurotoxicity and cytokine secretion by ligands of the cannabinoid-type CB2 receptor Br J Pharmacol. 139, 775-86 (2003).
19. Kogan N M, Mechoulam R. The chemistry of endocannabinoids. J. Endocrinol. Investig. 29 (Suppl. 3) 3-14 (2006).
20. Kogan, N M, Mechoulam, R. Cannabinoids in health and disease. Dialogues Clin. Neurosci. 9, 413-430 (2007).
21. Lotersztajn S, Teixeira-Clerc F, Julien B, Deveaux V, Ichigotani Y, Manin S, Tran-Van-Nhieu J, Karsak M, Zimmer A, Mallat A. CB2 receptors as new therapeutic targets for liver diseases. Brit. J. Pharmacol., 153, 286-289 (2008).
22. McMurry J E, Scott W J. A method for the regiospecific synthesis of enol triflates by enolate trapping. Tetrahedron Lett. 24, 979-982 (1983).
23. Mechoulam R, Braun P, Gaoni Y. Syntheses of Δ1-THC and related cannabinoids. J. Am. Chem. Soc., 94, 6159-6165 (1972).
24. Mechoulam R, Sumariwalla P F, Feldmann M, Galilly R. Cannabinoids in models of chronic inflammatory conditions. Phytochem. Revs 4, 11-18 (2005).
25. Ofek O, Karsak, M, Leclerc N, Fogel M, Frenkel B, Wright K, Tam J, Attar-Namdar M, Kram V, Shohami E, Mechoulam R, Zimmer A, Bab I. Peripheral CB2 cannabinoid receptor regulates bone mass. Proc. Natl. Acad. Sci., Proc. Natl. Acad. Sci. (US) 103, 696-701 (2006).
26. Pacher P, Haskó G. Endocannabinoids and cannabinoid receptors in ischaemia-reperfusion injury and preconditioning. Br J Pharmacol. 153:252-62 (2008).
27. Palazuelos J, Aquado T, Egia A, Mechoulam R, Guzman M, Galve-Roperh I. Non-psychoactive CB2 cannabinoid agonists stimulate neural progenitor proliferation. FASEB J. 580, 4337-4345 (2006).
28. Palazuelos J, Davoust N, Julien B, Hatterer E, Aguado T, Mechoulam R, Benito C, Romero J, Silva A, Guzman M, Nataf S, Galve-Roperh I. The CB2 cannabinoid receptor controls myeloid progenitor trafficking. Involvement in the pathogenesis of an animal model of multiple sclerosis. J Biol Chem. 283, 13320-13329 (2008).
29. Steffens S, Mach F. Cannabinoid receptors in atherosclerosis. Curr. Opinion Lipidology, 17, 519-526, 2006.
30. Steffens S, Veillard N R, Arnaud C, Pelli G, Burger F, Staub C, Karsak M, Zimmer A, Frossard J L, Mach F. Low dose oral cannabinoid therapy reduces progression of atherosclerosis in mice. Nature 434, 782-786 (2005).
31. Thoren S. 4 Isomeric alpha-hydroxybornanones. Acta Chemica Scandinavica. 24, 93-98 (1970).
32. van Sickle M D, Duncan M, Kingsley P J, Mouihate A, Urbani P, Mackie K, Stella N, Makriyannis A, Piomelli D, Davison J S, Mundt L J, Di Marzo V, Pittman Q J, Patel K D, Sharkey K A. Identification and functional characterization of brain stem cannabinoid CB2 receptors. Science, 310, 329-332 (2005).

33. Yamamoto W, Mikami T, Iwamura H. Involvement of central cannabinoid CB2 receptor in reducing mechanical allodynia in a mouse model of neuropathic pain. Eur. J. Pharmacol. 583, 56-61 (2008).

34. Zhang M, Martin B R, Adler M W, Razdan R K, Ganea D, Tuma R F. Modulation of the balance between cannabinoid CB1 and CB2 receptor activation during cerebral ischemic/reperfusion injury. Neurosci. 152, 753-760 (2008).

35. Pertwee R G, Gibson T M, Stevenson L A, Ross R A, Banner W K, Saha B, Razdan R K and Martin B R. O-1057, a potent water-soluble cannabinoid receptor agonist with antinociceptive properties. Br J Pharmacol. 129, 1577-1584 (2000).

36. Shohami E, Gallily R, Mechoulam R, Bass R and Ben-Hur T. Cytokine production in the brain following closed head injury: dexanabinol_HU-211/is a novel TNF-a inhibitor and an effective neuroprotectant. J. Neuroimmunol. 72, 169-177 (1997).

37. Ross R A, Brockie H C, Stevenson L A, Murphy V L, Templeton F, Makriyannis A and Pertwee R G. Agonist-inverse agonist characterization at CB1 and CB2 cannabinoid receptors of L759633, L759656 and AM630. Br J Pharmacol. 126, 665-672 (1999).

38. Beni-Adani L, Gozes I, Cohen Y, Assaf Y, Steingart R A, Brenneman D E, Eizenberg O, Trembolver V and Shohami E. A peptide derived from activity-dependent neuroprotective protein (ADNP) ameliorates injury response in closed head injury in mice. J Pharmacol Exp Ther. 296, 57-63 (2001).

Two cannabinoid receptors have been well characterized so far—the CB1 receptor, which is present mainly in the central nervous system (CNS), (and to a lesser extent in the periphery), and the CB2 receptor which is considered mainly a peripheral receptor. Natural stimulation of the CB1 receptor, which is produced by the endogenous cannabinoids, when and where needed, is central to many of our physiological systems. However exogenous administration of CB1 agonists (such as the marijuana constituent THC) may lead to undesirable side effects. Therefore CB1 agonists, which act on the central nervous system, are of limited therapeutic value (for a recent review see Kogan and Mechoulam, 2007).

The CB2 receptor is present in low levels in the CNS, mainly in glial cells. However, numerous neurological conditions have been shown to induce expression of this receptor in the brain. Some of these conditions are cerebral hypoxia-ischemia, cerebral artery occlusion, Alzheimer's disease and Huntington's disease. It was further shown that stimulation of the CB2 receptor is not accompanied by undesirable CNS or other effects, such as major and/or detrimental psychoactive effects, usually associated with the stimulation of the CB1 receptor (Ashton and Glass, 2007).

There is therefore a need for selective CB2 receptor stimulants, capable of being utilized for treating diseases, disorders or conditions associated with, or benefiting from such stimulation of CB2 receptors.

SUMMARY OF THE INVENTION

The present invention provides a compound of general formula (I):

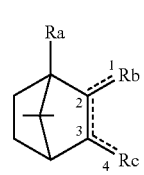

wherein

1═══2, 2═══3, 3═══4 are each independently a single or double bond;

$R_a$ is selected from straight or branched $C_1$-$C_5$ alkyl, straight or branched $C_2$-$C_5$ alkenyl, straight or branched $C_2$-$C_5$ alkynyl and —C(═O)$R_d$, each optionally substituted by at least one group selected from —OH, —COOH, —NH$_2$, $C_1$-$C_5$ amine, halogen, phenyl, heteroaryl; wherein $R_d$ is selected from the group consisting of —H, —OH, straight or branched $C_1$-$C_5$ alkyl, straight or branched $C_2$-$C_5$ alkenyl, straight or branched $C_2$-$C_5$ alkynyl, straight or branched $C_1$-$C_5$ alkoxy, —NR$_e$R$_f$;

$R_e$ and $R_f$ are each independently selected from H and straight or branched $C_1$-$C_5$ alkyl; and $R_b$ and $R_c$ are each independently selected from —H, —OH, ═O, ═CR$_g$R$_h$, ═NR$_i$, ═S, —$C_5$-$C_{15}$ aryl ring substituted by at least one group selected from a straight or branched $C_1$-$C_{12}$ alkyl, $C_2$-$C_{12}$ alkenyl, $C_2$-$C_{12}$ alkynyl, $C_1$-$C_{12}$ alkoxy, amine, $C_1$-$C_{12}$ alkoxycarboxylic acid, —OH, —OC(═O)$R_p$ and —C(═O)$R_q$; wherein $R_g$, $R_h$, $R_p$ and $R_q$ are each independently selected from H, straight or branched $C_1$-$C_5$ alkyl, straight or branched $C_1$-$C_5$ alkoxy and NH$_2$; and provided that at least one of $R_b$ and $R_c$ is said substituted —$C_5$-$C_{15}$ aryl ring.

In some embodiments of the invention at least one of 1═══2, 2═══3, 3═══4 is a double bond.

In one embodiment of the present invention, 2═══3 of compound of formula (I) is a double bond. Consequently, compound of formula (I) is a compound of formula (I'):

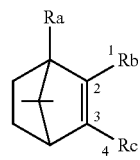

wherein substituents $R_a$, $R_b$ and $R_c$ are as defined herein above.

In another embodiment of the present invention, 2═══3 of a compound of formula (I) is a single bond. Consequently, compound of formula (I) is a compound of formula (I"):

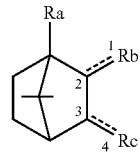

wherein substituents $R_a$, $R_b$ and $R_c$ are as defined herein above.

In one embodiment, 1═══2 is a double bond. According to this embodiment, 2═══3 is a single bond and 3═══4 may be either a single or double bond.

In another embodiment, 3═══4 is a double bond. According to this embodiment, 2═══3 is a single bond and 1═══2 may be either a single or double bond.

In a further embodiment 1═══2 is a single bond and 3═══4 is a single bond.

In another embodiment of the invention, at least one of $R_b$ and $R_c$ is a phenyl ring substituted by at least two substituent selected from a straight or branched $C_1$-$C_{12}$ alkyl, $C_2$-$C_{12}$ alkenyl, $C_2$-$C_{12}$ alkynyl, $C_1$-$C_{12}$ alkoxy, $C_1$-$C_{12}$ alkoxycarboxylic acid, —C(═O)OH, —C(═O)NH$_2$, —C(═O)($C_1$-$C_5$alkyl), —C(═O)($C_1$-$C_5$alkoxy), —OC(═O)H, —OC(═O)NH$_2$, —OC(═O)($C_1$-$C_5$alkyl). Thus, in one embodiment $R_b$ is a phenyl ring substituted by at least two substituent selected from a straight or branched $C_1$-$C_{12}$ alkyl, $C_2$-$C_{12}$ alkenyl, $C_2$-$C_{12}$ alkynyl, $C_1$-$C_{12}$ alkoxy, amine, $C_1$-$C_{12}$ alkoxycarboxylic acid, —COOH, —CONH$_2$, —C(═O)($C_1$-$C_5$alkyl), —C(═O)($C_1$-$C_5$alkoxy), —OCOH, —OC(═O)NH$_2$, —OC(═O)($C_1$-$C_5$alkyl) and $R_c$ is selected from —H, —OH, ═O, ═C$R_g$$R_h$, ═N$R_i$, ═S, —$C_5$-$C_{15}$ aryl ring substituted by at least one group selected from a straight or branched $C_1$-$C_{12}$ alkyl, $C_2$-$C_{12}$ alkenyl, $C_2$-$C_{12}$ alkynyl, $C_1$-$C_{12}$ alkoxy, amine, $C_1$-$C_{12}$ alkoxycarboxylic acid, —OC(═O)$R_p$ and —C(═O)$R_q$; wherein $R_g$, $R_h$, $R_i$ $R_p$ and $R_q$ are each independently selected from H, straight or branched $C_1$-$C_5$ alkyl, straight or branched $C_1$-$C_5$ alkoxy and NH$_2$. In another embodiment, $R_c$ is a phenyl ring substituted by at least two substituent selected from a straight or branched $C_1$-$C_{12}$ alkyl, $C_2$-$C_{12}$ alkenyl, $C_2$-$C_{12}$ alkynyl, $C_1$-$C_{12}$ alkoxy —COOH, —CONH$_2$, —C(═O)($C_1$-$C_5$alkyl), —C(═O)($C_1$-$C_5$alkoxy), —OCOH, —OC(═O)NH$_2$, —OC(═O)($C_1$-$C_5$alkyl) and $R_b$ is selected from —H, —OH, ═O, ═C$R_g$$R_h$, ═N$R_i$, ═S, —$C_5$-$C_{15}$ aryl ring substituted by at least one group selected from a straight or branched $C_1$-$C_{12}$ alkyl, $C_2$-$C_{12}$ alkenyl, $C_2$-$C_{12}$ alkynyl, $C_1$-$C_{12}$ alkoxy, amine, $C_1$-$C_{12}$ alkoxycarboxylic acid, —OC(═O)$R_p$ and —C(═O)$R_q$; wherein $R_g$, $R_h$, $R_i$ $R_p$ and $R_q$ are each independently selected from H, straight or branched $C_1$-$C_5$ alkyl, straight or branched $C_1$-$C_5$ alkoxy and —NH$_2$.

In another embodiment of the invention, at least one of $R_b$ and $R_c$ is a phenyl ring substituted by at least three substituent selected from a straight or branched $C_1$-$C_{12}$ alkyl, $C_2$-$C_{12}$ alkenyl, $C_2$-$C_{12}$ alkynyl, $C_1$-$C_{12}$ alkoxy, —C(═O)OH, —C(═O)NH$_2$, —C(═O)($C_1$-$C_5$alkyl), —C(═O)($C_1$-$C_5$alkoxy), —OC(═O)H, —OC(═O)NH$_2$, —OC(═O)($C_1$-$C_5$alkyl).

In some embodiments of the invention when all of 1═══2, 2═══3, 3═══4 represent a single bond, at least one of $R_b$ and $R_c$ is a —$C_5$-$C_{15}$ aryl ring being substituted by at least two substituents selected from a straight or branched $C_1$-$C_{12}$ alkyl, $C_2$-$C_{12}$ alkenyl, $C_2$-$C_{12}$ alkynyl, $C_1$-$C_{12}$ alkoxy, amine, $C_1$-$C_{12}$ alkoxycarboxylic acid, —OC(═O)$R_p$ and —C(═O)$R_q$; wherein $R_g$, $R_h$, $R_i$, $R_p$ and $R_q$ are each independently selected from H, straight or branched $C_1$-$C_5$ alkyl, straight or branched $C_1$-$C_5$ alkoxy and NH$_2$.

In other embodiments, of the invention when all of 1═══2, 2═══3, 3═══4 represent a single bond, at least one of $R_b$ and $R_c$ is a —$C_5$-$C_{15}$ aryl ring being substituted by at least three substituents selected from a straight or branched $C_1$-$C_{12}$ alkyl, $C_2$-$C_{12}$ alkenyl, $C_2$-$C_{12}$ alkynyl, $C_1$-$C_{12}$ alkoxy, amine, $C_1$-$C_{12}$ alkoxycarboxylic acid, —OC(═O)$R_p$ and —C(═O)$R_q$; wherein $R_g$, $R_h$, $R_i$, $R_p$ and $R_q$ are each independently selected from H, straight or branched $C_1$-$C_5$ alkyl, straight or branched $C_1$-$C_5$ alkoxy and NH$_2$ In another embodiment of the present invention, at least one of $R_b$ and $R_c$ is a group of formula (II):

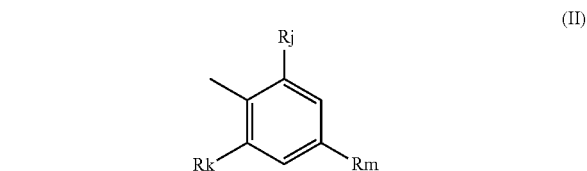

(II)

wherein $R_j$ and $R_k$ are each independently selected from H, and —O$R_n$ wherein $R_n$ is selected form H, —COO$R_t$, a straight or branched $C_1$-$C_5$ alkyl optionally substituted by at least one group selected from —COOH, —NH$_2$, provided that at least one of $R_j$ and $R_k$ is different than H; and $R_m$ is selected from a straight or branched $C_6$-$C_{12}$ alkyl, a straight or branched $C_5$-$C_9$ alkoxy, a straight or branched $C_1$-$C_7$ ether; each optionally substituted by at least one group selected from —COOH, —NH$_2$; and $R_t$ is selected from H, $C_1$-$C_5$ alkyl and —NH$_2$.

Thus, a compound of the invention may be a compound of any one formulae (III), (IV), (V) or (VI):

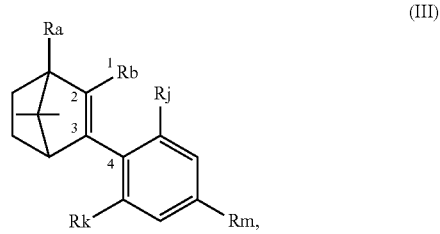

(III)

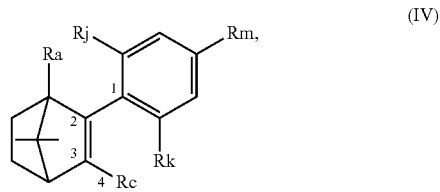

(IV)

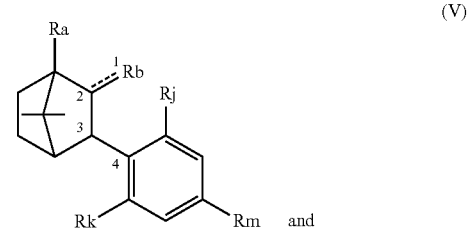

(V)

and

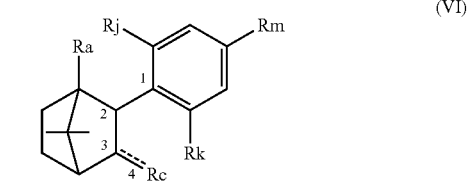

(VI)

wherein $R_j$ and $R_k$ are each independently H or —O$R_n$ wherein $R_n$ is selected from H, —COO$R_t$, a straight or branched $C_1$-$C_5$ alkyl optionally substituted by at least one group selected from —COOH, —NH$_2$, provided that at least one of $R_j$ and $R_k$ is different than H; and $R_m$ is a straight or branched $C_6$-$C_{12}$ alkyl and $R_t$ is selected from H, $C_1$-$C_5$ alkyl and —$NH_2$.

In another embodiment of the present invention, $R_a$ is selected from an straight or branched $C_1$-$C_5$ alkyl and —C(═O)$R_d$, each optionally substituted by at least one group selected from —OH, —COOH, —$NH_2$, $C_1$-$C_5$ amine, halogen, phenyl, heteroaryl and $R_d$ is as defined herein above.

In another embodiment of the present invention, at least one of $R_b$ and $R_c$ is a group of formula (II') or (II"):

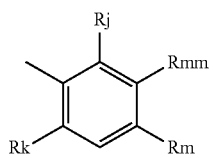

(II')

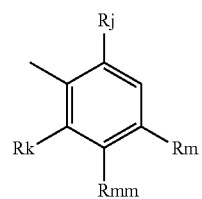

(II")

wherein $R_j$, $R_k$ and $R_{mm}$ are each independently selected from H, and —$OR_n$ wherein $R_n$ is selected form H. —$COOR_t$, a straight or branched $C_1$-$C_5$ alkyl optionally substituted by at least one group selected from —COOH, —$NH_2$, provided that at least one of $R_j$ and $R_k$ is different than H; and $R_m$ is selected from an optionally substituted straight or branched $C_3$-$C_{12}$ alkyl, an optionally substituted straight or branched $C_5$-$C_9$ alkoxy, an optionally substituted straight or branched $C_1$-$C_7$ ether; and $R_t$ is selected from H, $C_1$-$C_5$ alkyl and —$NH_2$.

In a further embodiment of a compound of formula (I), when 2═══3 is a single bond, $R_b$ and $R_c$ are each independently selected from —H, —OH, ═O, ═$CR_gR_h$, ═$NR_i$, ═S, —$C_5$-$C_{15}$ aryl ring substituted by at least two substituent selected from a straight or branched $C_1$-$C_{12}$ alkyl, $C_2$-$C_{12}$ alkenyl, $C_2$-$C_{12}$ alkynyl, $C_1$-$C_{12}$ alkoxy, amine, —OC(═O)$R_p$ and —C(═O)$R_q$; wherein $R_g$, $R_h$, $R_i$, $R_p$ and $R_q$ are each independently selected from H, straight or branched $C_1$-$C_5$ alkyl, straight or branched $C_1$-$C_5$ alkoxy and —$NH_2$; and provided that at least one of $R_b$ and $R_c$ is said substituted —$C_5$-$C_{15}$ aryl ring. In a further embodiment, said $R_b$ is ═O, thus a compound of the invention may be a compound of formula (VII), wherein $R_c$ is said substituted —$C_5$-$C_{15}$ aryl ring:

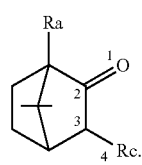

(VII)

In yet a further embodiment, $R_c$ is ═O, thus a compound of the invention may be a compound of formula (VIII), wherein $R_b$ is said substituted —$C_5$-$C_{15}$ aryl ring:

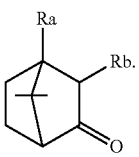

(VIII)

In one embodiment, a compound of the invention is selected from the following list:

methyl-2-(2,6-dimethoxy-4-(2-methyloctan-2-yl)phenyl)-7,7-dimethylbicyclo[2.2.1]hept-2-ene-1-carboxylate;

methyl-2-(2,6-dimethoxy-4-pentylphenyl)-7,7-dimethylbicyclo[2.2.1]hept-2-ene-1-carboxylate;

2-(2,6-dimethoxy-4-(2-methyloctan-2-yl)phenyl)-1,7,7-trimethylbicyclo[2.2.1]hept-2-ene;

(2-(2,6-dimethoxy-4-(2-methyloctan-2-yl)phenyl)-7,7-dimethylbicyclo[2.2.1]hept-2-en-1-yl)methanol;

(2-(2,6-dimethoxy-4-pentylphenyl)-7,7-dimethylbicyclo[2.2.1]hept-2-en-1-yl)methanol;

2-(2,6-dimethoxy-4-(2-methyloctan-2-yl)phenyl)-7,7-dimethylbicyclo[2.2.1]hept-2-ene-1-carboxylic acid;

2-(2,6-dimethoxy-4-pentylphenyl)-7,7-dimethylbicyclo[2.2.1]hept-2-ene-1-carboxylic acid;

3-(2,6-dimethoxy-4-(2-methyloctan-2-yl)phenyl)-1,7,7-trimethylbicyclo[2.2.1]hept-2-ene;

3-(2,6-dimethoxy-4-pentylphenyl)-1,7,7-trimethylbicyclo[2.2.1]heptan-2-one;

3-(2,6-dimethoxy-4-(2-methyloctan-2-yl)phenyl)-1,7,7-trimethylbicyclo[2.2.1]heptan-2-one;

3-(2,6-dimethoxy-4-pentylphenyl)-1,7,7-trimethylbicyclo[2.2.1]heptan-2-ol;

3-(2,6-dimethoxy-4-(2-methyloctan-2-yl)phenyl)-1,7,7-trimethylbicyclo[2.2.1]heptan-2-ol (3-(2,6-dimethoxy-4-(2-methyloctan-2-yl)phenyl)-7,7-dimethylbicyclo[2.2.1]hept-2-en-1-yl)methanol;

3-(2,6-dimethoxy-4-(2-methyloctan-2-yl)phenyl)-7,7-dimethylbicyclo[2.2.1]hept-2-ene-1-carboxylic acid;

methyl 3-(2,6-dimethoxy-4-(2-methyloctan-2-yl)phenyl)-7,7-dimethylbicyclo[2.2.1]hept-2-ene-1-carboxylate;

(3-(2,6-dimethoxy-4-pentylphenyl)-7,7-dimethylbicyclo[2.2.1]hept-2-en-1-yl)methanol;

3-(2,6-dimethoxy-4-pentylphenyl)-7,7-dimethylbicyclo[2.2.1]hept-2-ene-1-carboxylic acid;

5-(2-methyloctan-2-yl)-2-(4,7,7-trimethylbicyclo[2.2.1]hept-2-en-2-yl)benzene-1,3-diol;

2-(4-(hydroxymethyl)-7,7-dimethylbicyclo[2.2.1]hept-2-en-2-yl)-5-(2-methyloctan-2-yl)benzene-1,3-diol;

3-(2,6-dihydroxy-4-(2-methyloctan-2-yl)phenyl)-7,7-dimethylbicyclo[2.2.1]hept-2-ene-1-carboxylic acid;

2-(4-(hydroxymethyl)-7,7-dimethylbicyclo[2.2.1]heptan-2-yl)-5-(2-methyloctan-2-yl)benzene-1,3-diol;

5-(2-methyloctan-2-yl)-2-(4,7,7-trimethylbicyclo[2.2.1]heptan-2-yl)benzene-1,3-diol; and 3-(2,6-dihydroxy-4-(2-methyloctan-2-yl)phenyl)-7,7-dimethylbicyclo[2.2.1]heptane-1-carboxylic acid.

The invention further provides a compound of general formula (I):

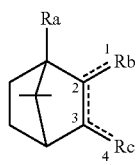

(I)

wherein

1═2, 2═3, 3═4 are each independently a single or double bond;

$R_a$ is selected from an straight or branched $C_1$-$C_5$ alkyl, straight or branched $C_2$-$C_5$ alkenyl, straight or branched $C_2$-$C_5$ alkynyl and —C(═O)$R_d$, each optionally substituted by at least one group selected from —OH, —COOH, —NH$_2$, $C_1$-$C_5$ amine, halogen, phenyl, heteroaryl; wherein $R_d$ is selected from the group consisting of —H, —OH, straight or branched $C_1$-$C_5$ alkyl, straight or branched $C_2$-$C_5$ alkenyl, straight or branched $C_2$-$C_5$ alkynyl, straight or branched $C_1$-$C_5$ alkoxy, —NR$_e$R$_f$;

$R_e$ and $R_f$ are each independently selected from H and straight or branched $C_1$-$C_5$ alkyl; and $R_b$ and $R_c$ are each independently selected from —H, —OH, ═O, ═CR$_g$R$_h$, ═NR$_i$, ═S, —$C_5$-$C_{15}$ aryl ring substituted by at least one group selected from a straight or branched $C_1$-$C_{12}$ alkyl, $C_2$-$C_{12}$ alkenyl, $C_2$-$C_{12}$ alkynyl, $C_1$-$C_{12}$ alkoxy, amine, $C_1$-$C_{12}$ alkoxycarboxylic acid, —OH, —OC(═O)$R_p$ and —C(═O)$R_q$; wherein $R_g$, $R_h$, $R_i$, $R_p$ and $R_q$ are each independently selected from H, straight or branched $C_1$-$C_5$ alkyl, straight or branched $C_1$-$C_5$ alkoxy and —NH$_2$;

or $R_a$ and $R_b$ may form a ring together with the carbon atoms they are each attached to; said ring may be a cycloalkyl, cycloheteroalkyl, cycloheteroalkenyl, cycloalkenyl, cycloalkynyl, cycloheteroalkynyl ring; in some embodiments said ring is a 6 to 12 member ring;

provided that at least one of $R_b$ and $R_c$ is said substituted —$C_5$-$C_{15}$ aryl ring.

In some embodiments, a compound of the invention has the general formula (XII):

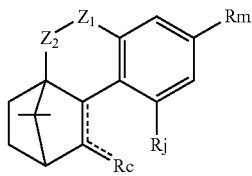

(XII)

wherein ═ is a single or double bond;

$R_c$ is selected from —H, —OH, ═O, ═CR$_g$R$_h$, ═NR$_i$, ═S, —$C_5$-$C_{15}$ aryl ring substituted by at least one group selected from a straight or branched $C_1$-$C_{12}$ alkyl, $C_2$-$C_{12}$ alkenyl, $C_2$-$C_{12}$ alkynyl, $C_1$-$C_{12}$ alkoxy, amine, $C_1$-$C_{12}$ alkoxycarboxylic acid, —OC(═O)$R_p$ and —C(═O)$R_q$; wherein $R_g$, $R_h$, $R_i$, $R_p$ and $R_q$ are each independently selected from H, straight or branched $C_1$-$C_5$ alkyl, straight or branched $C_1$-$C_5$ alkoxy and —NH$_2$;

$R_j$ is selected from H, and —OR$_n$ wherein $R_n$ is selected form H, —COOR$_t$, a straight or branched $C_1$-$C_5$ alkyl optionally substituted by at least one group selected from —COOH, —NH$_2$; and $R_t$ is selected from H, $C_1$-$C_5$ alkyl and —NH$_2$;

$R_m$ is selected from a straight or branched $C_6$-$C_{12}$ alkyl, a straight or branched $C_5$-$C_9$ alkoxy, a straight or branched $C_1$-$C_7$ ether; each optionally substituted by at least one group selected from —COOH, —NH$_2$;

$Z_1$ and $Z_2$ are each independently selected from —O—, straight or branched $C_1$-$C_5$-alkylene, —S—, —C(═O)— and —C(═S)—.

In other embodiments, a compound of the invention may be selected from the group consisting of:

(26)

(27)

(28)

(29)

As used herein, the term "alkyl" refers to a straight or branched chain hydrocarbon having from one to five carbon atoms, or from one to seven carbon atoms, or from five to nine carbon atoms, or from six to twelve carbon atoms. Examples of "alkyl" as used herein include, but are not limited to, methyl, ethyl, propyl, n-butyl, n-pentyl, isobutyl, and isopropyl, tert-butyl, and the like.

As used herein, the term "alkenyl" represents a branched or straight hydrocarbon group having from 2 to 5 or from 2 to 12 carbon atoms and at least one double bond. Examples of such groups include, but are not limited to, ethenyl, 1-propenyl, 2-propenyl, isopropenyl, 1,3-butadienyl, 1-butenyl, 2-butenyl, 1-pentenyl, 2-pentenyl, 1-hexenyl, 2-hexenyl and the like.

As used herein, the term "alkynyl" represents a branched or straight hydrocarbon group having from 2 to 5 or from 2 to 12 carbon atoms and at least one triple bond. Examples of such groups include, but are not limited to, ethynyl, 1-propynyl, 2-propynyl, 1-butynyl, 2-butynyl, 1-pentynyl, 2-pentynyl, 1-hexynyl, 2-hexynyl and the like.

As used herein the term "aryl" refers to aromatic monocyclic or multicyclic groups containing from 5 to 15 carbon atoms. Aryl groups include, but are not limited to groups such as unsubstituted or substituted fluorenyl, unsubstituted or substituted phenyl, and unsubstituted or substituted naphthyl. When referring to said aryl being substituted, said substitution may be at any position on the ring, other than the point of attachment to the other ring system of a compound of the invention. Therefore, any hydrogen atom on the aryl ring may be substituted with a substituent defined by the invention. In embodiments where the aryl is a phenyl ring, said substitution may be at the meta- and/or ortho- and/or para-position relative to the point of attachment.

As used herein the term "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl, As used herein, the term "$C_1$-$C_{12}$ alkoxycarboxylic acid" refers to a —O—($C_1$-$C_{12}$ alkylene)-COOH radical.

As used herein the term "alkylene" refers to a saturated, divalent, branched or straight hydrocarbon group having from one to five carbon atoms. Non-limiting examples of $C_{1-5}$-alkylene groups include, methylene, ethylene, 1,2-propylene, 1,3-propylene, butylene, isobutylidene, pentylene, hexylene and the like.

As used herein the term "ester" is meant to encompass an —COOR group wherein R is an alkyl as defined herein above.

A used herein the term "ether" refers to an —R'OR group, wherein R' is a $C_1$-$C_7$ straight or branched alkylene group and R is a $C_1$-$C_7$ straight or branched alkyl group.

As used herein, the term "alkoxy" refers to an RO— group, where R is alkyl as defined above.

As used herein the term "$C_1$-$C_7$ amide" refers to a monoalkyl amide (—CONHR) or dialkyl amide (—CONRR'), wherein R and R' are independently a $C_1$-$C_7$ straight or branched alkyl.

As used herein the term "$C_1$-$C_5$ amine" refers to an —NHR or —NRR' group wherein R and R' are independently a $C_1$-$C_5$ straight or branched alkyl.

The term "optionally substituted" as used herein means that the groups in question are either unsubstituted or substituted with one or more of the substituents such as for example those specified above and phenyl, substituted phenyl, aryl, heteroaryl, cycloalkyl, heterocycloalkyl, halogen (—F, —Cl, —Br, —I), —COOH, —NH$_2$, —NHR and —NRR' wherein R and R' are each independently a straight or branched $C_1$-$C_5$ alkyl. When the groups are substituted with more than one substituent the substituents may be the same or different and said substitution may occur at any position on the substituted group (i.e. at a terminal or any mid-chain position or both).

The term "cycloalkyl" refers to a cyclic ring having from 6 to 12 carbon atoms connected via single bond only.

The term "cycloalkenyl" refers to a cyclic ring having from 6 to 12 carbon atoms connected having at least one double bond.

The term "cycloalkynyl" refers to a cyclic ring having from 6 to 12 carbon atoms connected having at least one triple bond.

The term "cycloheteroalkyl" refers to a cyclic ring having from 6 to 12 carbon atoms connected via single bond only, wherein at least one carbon atom is replaced with a heteroatom selected from N, O, S.

The term "cycloheteroalkenyl" refers to a cyclic ring having from 6 to 12 carbon atoms connected having at least one double bond, wherein at least one carbon atom is replaced with a heteroatom selected from N, O, S.

The term "cycloheteroalkynyl" refers to a cyclic ring having from 6 to 12 carbon atoms connected having at least one triple bond, wherein at least one carbon atom is replaced with a heteroatom selected from N, O, S.

It is appreciated by a person skilled in the art that certain compounds of the invention may posses at least one stereogenic carbon atom. Thus, it should be noted that the present invention encompasses all possible stereosiormers of such compounds including all possible mixtures thereof (such as for example racemic mixtures, diastereomeric mixtures, non-racemic mixtures etc.). It is further noted that compounds of the invention may posses a double bond. Thus, the present invention encompasses any stereoisomer (cis, trans, E or Z stereoisomers) of such compounds including any mixture thereof.

The invention further provides processes for the preparation of compounds of the invention.

In one aspect the invention provides a process for the preparation of a compound of general formula (I), as defined herein above, said process comprising:

(a) providing a compound having the general formula (X) or (X'):

(X)

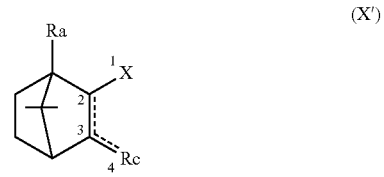

(X')

wherein $R_a$, $R_b$ and $R_c$ have the same meaning as defined herein above; X is a halide, pseudohalide, functional leaving group (such as for example —OTf and similar functional groups capable of being easily removed upon coupling reaction); and 1⚏2, 2⚏3, 3⚏4 are each independently a single or double bond;

(b) reacting compound (X) or (X') with a compound having the general formula (XI) or (XI') respectively:

(XI')

-continued (XI)

Rb—B(Y)(Y)

wherein each of Y is selected from OH, $C_1$-$C_5$ alkoxy or both may form a cyclic dialkoxy ring together with the boron atom they are attached to, in the presence of a catalyst; thereby obtaining a compound of formula (I).

In another aspect the invention provides a process for the preparation of a compound of general formula (I), as defined herein above, said process comprising:

(a) providing a compound having the general formula (X) or (X'):

(X)

(X')

wherein $R_a$, $R_b$ and $R_c$ have the same meaning as defined herein above; X is a halide, pseudohalide, functional leaving group (such as for example —OTf and similar functional groups capable of being easily removed upon coupling reaction); and 1⋯2, 2⋯3, 3⋯4 are each independently a single or double bond;

(b) coupling compound (X) or (X') with $R_c$—H or $R_b$—H respectively; thereby obtaining a compound of formula (I). In some embodiments said coupling process is a halogen-metal exchange process, as detailed herein below.

Such processes include for example Suzuki cross-coupling reactions as follows:

1. Methylation of (±) ketopinic acid with methyl iodide and potassium carbonate in dimethylformamide thereby obtaining (±) methyl ketopinate;
2. Enolization of (±) camphor/(±) epicamphor/(±) methyl ketopinate by lithium diisopropylamide and the addition of phenyl triflimide in tetrahydrofuran to afford corresponding (±) vinyl triflate;
3. Lithiation of 2,6-dimethyl ether-4-alkyl resorcinol by n-butyl lithium and formation of aryl boronic ester using isopropyl pinacol borate in tetrahydrofuran;
4. Cross-coupling reaction between aryl boronic ester and (±) vinyl triflate catalyzed by tetrakis-palladium triphenyl phosphine in the presence of tert-butyl ammonium fluoride in tetrahydrofuran to obtain corresponding (±) arylated bornene;
5. Reduction of (±) arylated methyl ketopinate by lithium aluminium hydride in tetrahydrofuran to afford corresponding alcohol;
6. Hydrolisis of (±) arylated methyl ketopinate by lithium hydroxide in methanol/water to obtain corresponding acid.

Another alternative process for the manufacture of compounds of the invention include halogen-metal exchange process as follows:

1. Lithiation by n-butyl lithium and copper iodide metalation of 2,6-dimethyl ether-4-alkyl resorcinol promoted coupling reaction with (+) 3-bromocamphor in diethyl ether and dimethyl sulfoxide to obtain corresponding arylated camphor
2. Reduction of camphoric carbonyl by lithium aluminium hydride in tetrahydrofuran to afford corresponding alcohol.

Exemplary synthetic procedures for the manufacture of compounds of the invention are described in Schemes 1 and 2.

Scheme 1a. Cross-coupling reaction at the C2-position of camphoric moiety.

1-$R_1$: 1',1'-dimethylheptyl
2-$R_1$: n-pentyl

3-$R_1$: 1',1'-dimethylheptyl(DMH)
4-$R_1$: n-pentyl($C_5H_{11}$)

5a-(1R,4S)
5b-(1S,4R)

6a-(1R,4S)
6b-(1S,4R)

7a-(1R,4S)
7b-(1S,4R)

7a-(1R,4S); R2: COOCH$_3$
7b-(1S,4R); R2: COOCH$_3$
8a-(1R,4R); R$_2$: CH$_3$
8b-(1S,4S); R$_2$: CH$_3$ 9a-(1R,4S); R2: COOCH$_3$
9b-(1S,4R); R2: COOCH$_3$
10a-(1R,4R); R$_2$: CH$_3$
10b-(1S,4S); R$_2$: CH$_3$

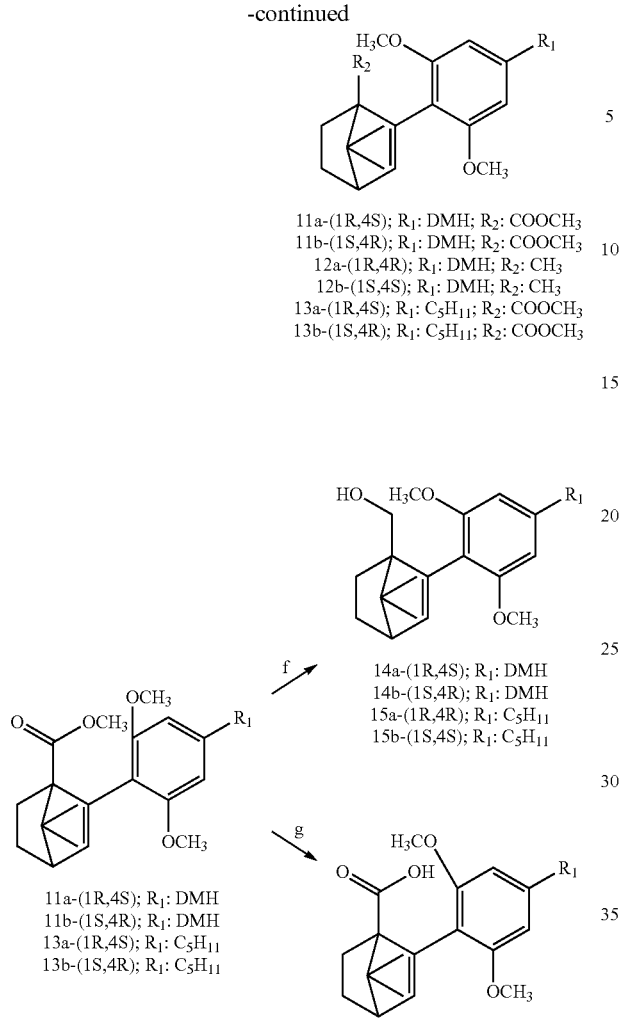

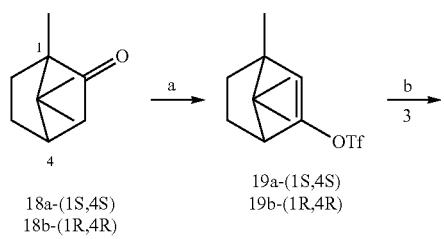

Scheme 2ᵃ. Cross-coupling reactions substituted at C3-position of camphoric moiety.

ᵃReagents and conditions:
(a) n-BuLi, THF, 0° C., PINBOP, -78° C.
(b) Na₂CO₃, H₂O, KMnO₄, reflux.
(c) K₂CO₃, DMF, MeI, r.t.
(d) LDA, THF, -78° C., phenyl triflimide, 0° C. to r.t.
(e) Pd(PPh₃)₄, t-BuNF, THF, reflux.
(f) LiAlH₄, THF, 0° to r.t.
(g) LiOH, MeOH/H₂O 3:1, 200° C.

ᵃReagents and conditions:
(a) LDA, THF, -78° C., phenyl triflimide, 0° C. to r.t.
(b) Pd(PPh₃)₄, t-BuNF, THF, reflux.
(c) n-BuLi, diethyl ether, 0° C. to r.t., CuI, diethyl ether/DMSO.
(d) LiAlH₄, diethyl ether, 0° C. to reflux.

In a further embodiment a compound of the invention is capable of stimulating a CB receptor.

The term "CB receptor" is meant to encompass a cannabinoid G-protein coupled receptor, defined by their capability to bind to cannabinoids and/or endocannabinoids. In one embodiment said receptor is a CB2 receptor (cannabinoid receptor Type 2). In another embodiment said stimulation of a CB2 receptor is associated with the treatment of a disease, disorder or condition.

When referring to "stimulation" of a composition of the invention to a CB receptor it is meant to include any degree of excitation of a CB receptor to allow activation of said receptor, such as for example agonistic effect of a compound of the invention on said CB receptor. It is noted that in order for such a stimulation to be achieved an association between a compound of the invention and said receptor should be established. A compound of the present invention may be associated with said receptor via any type of interaction such as for example covalent bonding, electrostatic bonding (such as for example hydrogen bonding, π or σ interactions, London dispersion forces, Van-Der-Waals forces etc.), ionic bonding, metallic bonding etc.

CB2 receptor stimulation has been shown to be of considerable medical value (Ashton and Glass, 2007). Some effects relevant to our patent are listed below:

1. Selective CB2 receptor stimulation causes potent anti-inflammatory effects in a diverse range of animal models (Ashton and Glass, 2007; Benito et al. 2008); lowers neuropathic pain (Yamamoto et al., 2008); inhibits secretion of pro-inflammatory cytokines (Klegeris et al., 2003).
2. CB2 receptor agonists stimulate osteoblast function and inhibit osteoclasts leading to increased bone formation. These effects are of major relevance to osteoporosis (Ofek et al., 2005).
3. CB2 receptor stimulation retards progression of atherosclerosis in an animal model (Stefens et al., 2005; Steffens and Mach, 2006). As cerebral hypoxia-ischemia and middle cerebral artery occlusion induce expression of the CB2 receptor, such agonists may lower the effects of these conditions (Ashton et al., 2006).
4. Selective CB2 receptor stimulation has been shown to lower hepatic encephalopathy (a neuropsychiatric complication occurring in both acute and chronic liver failure) and to display anti-fibrinogenic effects (Avraham et al., 2006; Dagon et al., 2007; Lotersztajn et al., 2008).
5. CB2 receptor stimulation has the potential to block progression of Alzheimer's disease (Benito et al., 2008), Huntington's disease (Fernandez-Ruiz et al. 2005), amyotrophic lateral sclerosis (Bilsland et al., 2006; Centonze et al., 2007), multiple sclerosis (Docagne et al., 2008) and myelin disorders (Arevalo-Martin et al., 2008). For a general review see Fernandez-Ruiz et al., (2008).
6. Cannabinoid CB2 receptor activation decreases cerebral infarction in a mouse focal ischemia/reperfusion model and a CB1 antagonist together with a CB2 agonist improved cerebral blood flow (Zhang et al. 2008).
7. CB2 receptor stimulation helps the establishment of ischemic preconditioning (a potent endogenous form of tissue protection against ischemia-reperfusion in various organs) (Pacher and Hasko, 2008).
8. CB2 receptor stimulation causes inhibition of emesis (van Sickle et al., 2005).
9. CB2 cannabinoid agonists stimulate neural progenitor proliferation (Palazuelos et al., 2006, 2008). This effect may be associated with improvement of neural damage.

In the context of the present invention the term "treatment" is meant to encompass the management and care of a patient for the purpose of combating a disease, disorder or condition. The term is intended to include the delaying of the progression of a disease, disorder or condition, the alleviation or relief of symptoms and complications, and/or the cure or elimination of the disease, disorder or condition. The patient to be treated is preferably a mammal, in particular a human being. This term refers to the administration of a therapeutic amount of a compound of the invention which is effective in one of the following: ameliorating undesired symptoms associated with a disease, disorder, or pathological condition; effective in preventing the manifestation of such symptoms before they occur; effective in slowing down the progression of a disease or disorder; effective in slowing down the deterioration of a disease, disorder or condition; effective in prolonging the time period onset of remission period; effective in slowing down the irreversible damage caused in a progressive chronic stage of a disorder; effective to delay the onset of said progressive; effective to lessen the severity or cure the disease or disorder; effective to improve survival rates of individuals infected with the disease, or effective to prevent the disease form occurring altogether (for example in an individual generally prone to the disease) or a combination of two or more of the above.

Thus, in one embodiment of the present invention, said disease, disorder or condition is selected from inflammation, pain, allergies, neurological and neurodegenerative diseases, liver diseases, cerebral injury, cancer, retinal vascularization, endometritis, appetite related disorders, metabolic syndrome, diabetes, atherosclerosis; disorders related to anti-fibrinogenic effects, inflammatory bowel disease, arthritis and emesis, or any combination thereof.

In a further embodiment, said disease, disorder or condition is cerebral injury. In another embodiment said cerebral injury is brain trauma selected from closed head injury, penetrating head injury, blast injury, cerebral ischemic-reperfusion injury, post-operable brain injury, brain hemorrhaging.

In another embodiment said compound of the invention is capable of lowering the secondary damage produced by brain trauma.

The term "cerebral injury", "brain trauma" or "traumatic brain injury" as used herein interchangeably is meant to encompass any traumatical injury to the brain, which may be caused by an external impac force (such as rapid acceleration or deceleration, impact, blast waves, or penetration by a projectile) or by any disease or disorder (such as for example ischemia, stroke, infection or anyurism).

Brain trauma can be classified based on severity, mechanism (closed or penetrating head injury), or other features (e.g. occurring in a specific anatomical location or over a widespread area in the brain). Head injuries can also be classified into mild, moderate, and severe categories and may be diagnosed using different International scales measuring for example the level of consciousness of the injured subject.

In addition to the damage caused at the moment of injury, brain trauma causes secondary injury (secondary damage produced by brain trauma), which is manifested in a variety of events that take place within minutes and/or days following the injury. These processes, which include alterations in cerebral blood flow and the pressure within the skull, contribute substantially to the damage from the initial injury. As a result brain function may be temporarily or permanently impaired and structural damage may or may not be detectable.

Deterioration in brain function and neurological functions of the brain can be attributed not only to the primary brain injury (the damage that occurs at the moment of trauma when tissues and blood vessels are stretched, compressed, and torn) but rather, to the secondary injury, expressed by a complex set of cellular processes and biochemical cascades that occur in the minutes to days following the trauma. These secondary processes can dramatically worsen the damage caused by primary injury and account for the greatest number of permannet imparment and also deaths. Secondary events include but are not limited to damage to the blood—brain barrier, release of factors that cause inflammation, free radical overload, excessive release of the neurotransmitter glutamate (excitotoxicity), influx of calcium and sodium ions into neurons, and dysfunction of mitochondria. Injured axons in the brain's white matter may separate from their cell bodies as a result of secondary injury, potentially killing those neurons. Other factors in secondary injury are changes in the blood flow to the brain; ischemia (insufficient blood flow); cerebral hypoxia (insufficient oxygen in the brain); cerebral edema (swelling of the brain); and raised intracranial pressure (the pressure within the skull). Intracranial pressure may rise due to swelling or a mass effect from a lesion, such as a hemorrhage. As a result, cerebral perfusion pressure (the pressure of blood flow in the brain) is reduced; ischemia results. When the pressure within the skull is too high, it can cause brain death or herniation, in which parts of the brain are squeezed by structures in the skull.

In another embodiment, a compound of the invention is utilized for use as a medicament.

In a further embodiment, a compound of the invention is used in the treatment of disease, disorder or condition is selected from inflammation, pain, allergies, neurological and neurodegenerative diseases, liver diseases, cerebral injury, cancer, retinal vascularization, endometritis, appetite related disorders, metabolic syndrome, diabetes, atherosclerosis; disorders related to anti-fibrinogenic effects, inflammatory bowel disease, arthritis and emesis, or any combination thereof. In one embodiment, a compound of the invention is used in the treatment of cerebral injury. In one embodiment said cerebral injury is selected from closed head injury, penetrating head injury, blast injury, cerebral ischemic-reperfusion injury, post-operable brain injury, brain hemorrhaging. In another embodiment a compound of the invention is utilized for use in lowering secondary damage produced by brain trauma.

In another one of its aspects the invention provides a pharmaceutical composition comprising a compound of the invention.

In one embodiment said pharmaceutical composition of the invention is for use in the treatment of disease, disorder or condition is selected from inflammation, pain, allergies, neurological and neurodegenerative diseases, liver diseases, cerebral injury, cancer, retinal vascularization, endometritis, appetite related disorders, metabolic syndrome, diabetes, atherosclerosis; disorders related to anti-fibrinogenic effects, inflammatory bowel disease, arthritis and emesis, or any combination thereof. In another embodiment said disease, disorder or condition is cerebral injury. In a further embodiment said cerebral injury is selected from closed head injury, penetrating head injury, blast injury, cerebral ischemic-reperfusion injury, post-operable brain injury, brain hemorrhaging. In another embodiment a pharmaceutical composition of the invention is used in lowering secondary damage produced by brain trauma.

In a further aspect of the invention, there is provided a use of a compound of the invention, for the manufacture of a pharmaceutical composition.

In some embodiments said p pharmaceutical composition is for use in the stimulation of bone growth, bone mass, bone repair or prevention of bone loss.

In another aspect, the invention provides a use of a compound of the invention, for the manufacture of a medicament (or pharmaceutical composition) capable of stimulating a CB receptor. In one embodiment receptor is a CB2 receptor.

In a further aspect the invention provides a use of a compound of the invention, for the manufacture of a medicament for the treatment of cerebral injury.

In another aspect the invention provides a use of a compound of the invention, for the manufacture of a medicament for lowering secondary damage produced by brain trauma.

In another one of its aspects the invention provides a use of a compound of the invention, for the preparation of a pharmaceutical composition for stimulation of bone growth, bone mass, bone repair or prevention of bone loss.

In a further aspect of the invention there is provided a compound of the invention, for use in the stimulation of bone growth, bone mass, bone repair or prevention of bone loss.

In another one of its aspects the invention provides a method of stimulation of bone growth, bone mass, bone repair or prevention of bone loss, said method comprising administering to a subject in need thereof a therapeutically effective amount of at least one compound of the invention.

In some embodiments said stimulation of bone growth, bone mass, bone repair or prevention of bone loss is associated with the treatment of at least one disease or a disorder selected from osteopenia, osteoporosis, bone fracture or deficiency, primary or secondary hyperparathyroidism, osteoarthritis, periodontal disease or defect, an osteolytic bone loss disease, post-plastic surgery, post-orthopedic surgery, post oral surgery, post-orthopedic implantation, and post-dental implantation, primary and metastatic bone cancer, osteomyelitis, or any combinations thereof.

In other embodiments said at least one disease or disorder is selected from osteopenia and osteoporosis.

The term "stimulation of bone growth, bone mass, bone repair" is meant to encompass any quantitative and/or qualitative promotion of growth of the osseous tissue, any quantitative and/or qualitative promotion of mass of the osseous tissue and any quantitative and/or qualitative promotion of osseous tissue repair (for example in the case any part of the osseous tissue is damaged or fractured for example after impact or as a consequence of a disease, condition or any side effect of an external treatment) in vertebrates at any development stage (from embryonic stage to elderly). In some embodiments, the pharmaceutical composition is for increasing bone mass in a subject in need thereof. In other embodiments, the pharmaceutical composition is for promoting bone repair.

The term "prevention of bone loss" is meant to encompass any quantitative and/or qualitative deterrence of osseous tissue loss in vertebrates at any development stage (from embryonic development stage to elderly).

Non-limiting examples of medical conditions benefiting from stimulating bone growth, gain of bone mass, prevention and rescue of bone loss and bone repair are osteopenia, osteoporosis, bone fracture or deficiency, primary or secondary hyperparathyroidism, osteoarthritis, periodontal disease or defect, an osteolytic bone loss disease, post-plastic surgery, post-orthopedic surgery, post oral surgery, post-orthopedic implantation, and post-dental implantation, primary and metastatic bone cancer, osteomyelitis, or any combinations thereof. In some embodiments, a medical condition benefiting from stimulating bone growth is osteopenia or osteoporosis.

When referring to pharmaceutical compositions comprising a compound of the subject invention it should be understood to encompass admixtures of compounds of the invention, with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy. Such methods include the step of bringing in association compounds used in the invention or combinations thereof with any auxiliary agent.

Auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use.

For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The exact dose and regimen of administration of the composition will necessarily be dependent upon the therapeutic or nutritional effect to be achieved and may vary with the particular formula, the route of administration, and the age and condition of the individual subject to whom the composition is to be administered.

In a further aspect the invention provides a method for stimulating a CB receptor in a subject in need thereof, said method comprising administering to said subject a therapeutically effective amount of a compound of the invention. In one embodiment said CB receptor is a CB2 receptor.

In another one of its aspects the invention provides a method of treating a disease, disorder or condition is selected from inflammation, pain, allergies, neurological and neurodegenerative diseases, liver diseases, cerebral injury, cancer, retinal vascularization, endometritis, appetite related disorders, metabolic syndrome, diabetes, atherosclerosis; disorders related to anti-fibrinogenic effects, inflammatory bowel disease, arthritis and emesis, or any combination thereof, said method comprising administering to in a subject in need thereof an effective amount of a compound of the invention.

In a further aspect the invention provides a method of treating cerebral injury in a subject in need thereof, said method comprising administering to said subject an effective amount of a compound of the invention. In one embodiment said cerebral injury is selected from closed head injury, penetrating head injury, blast injury, cerebral ischemic-reperfusion injury, post-operable brain injury, brain hemorrhaging.

In a further aspect the invention provides a method of lowering secondary damage produced by brain trauma in a subject in need thereof, said method comprising administering to said subject an effective amount of a compound of the invention.

In a further aspect the invention provides a method of affecting the c-AMP formation in a subject in need thereof, said method comprising administering to said subject an effective amount of a compound of the invention.

When referring to the influence of a compound of the invention on the "affecting the c-AMP formation" it should be understood to encompass stimulation or inhibition of forskolin-induced c-AMP accumulation.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1A:
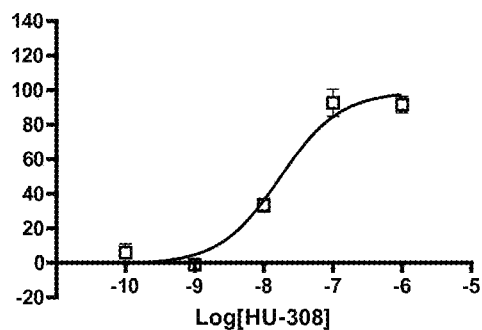
FIG. 1A-1G show the GTPγS binding graphs for human CB2 receptor of compounds of the invention: HU-308 (FIG. 1A), HU-909 (FIG. 1B), HU-910 (FIG. 1C), HU-911 (FIG. 1D), HU-913 (FIG. 1E), HU-926 (FIG. 1F) and HU-928 (FIG. 1G). Data is shown as [$^{35}$S]GTPγS binding normalised to maximal HU-308 binding under the same experimental conditions.
Figure 1B:
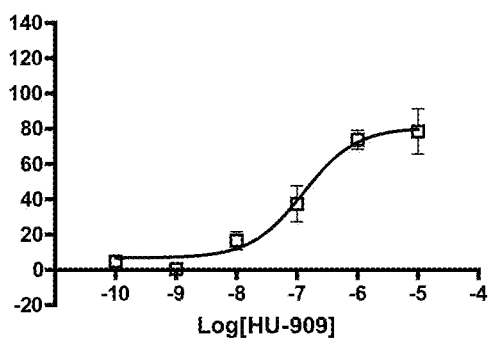
Figure 1C:
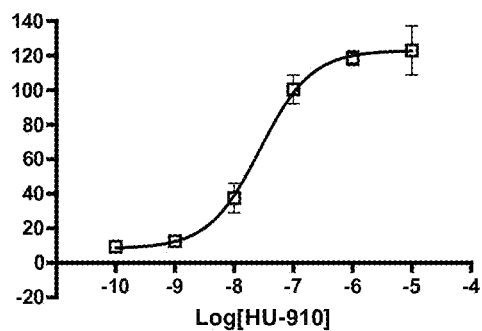
Figure 1D:
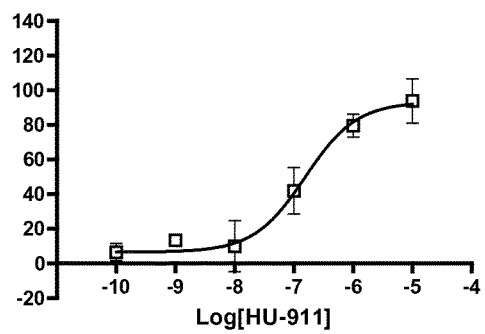
Figure 1E:
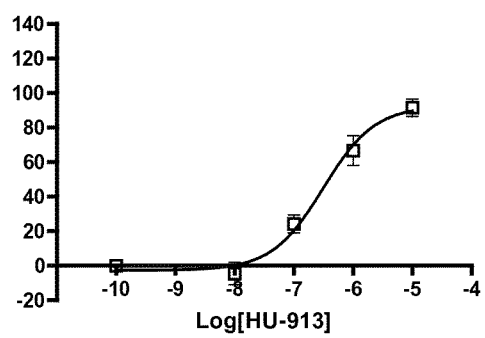
Figure 1F:
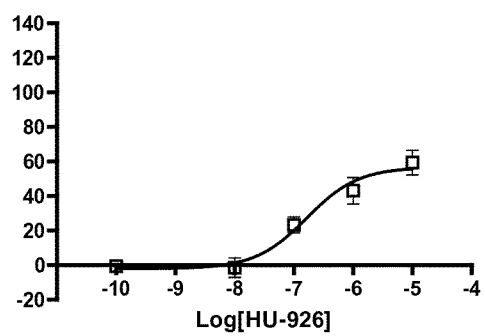

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

Example 1

Synthetic Preparations

Materials and Methods

All reagents were purchased from Sigma-Aldrich (Israel) and Acros (Israel) and used without further purification. (±)-Camphor and (+)-3-bromocamphor were purchased from Sigma-Aldrich (Israel). (±)-Camphor-10-sulfonyl chloride and (±)-camphorquinone were purchased from Acros (Israel).

All solvents were purchased from Bio-Lab (Israel).

All anhydrous reactions were performed under nitrogen atmosphere in flame-dried glassware using anhydrous solvents.

Silica gel 60 Å 0.063-0.2 mesh was purchased from BioLab (Israel) and used for column chromatography.

Preparative thin layer chromatography (TLC) was performed on PLC silica gel plates 60 Å $F_{254}$, 2 mm, purchased form Merck (Germany).

Purity of the intermediates and final compounds was established by analytical TLC on precoated aluminum silica gel 60, $F_{254}$, 200 μm, purchased from Merck (Germany) and chromatograms were visualized under ultraviolet light and by phosphomolybdic acid staining.

Melting points were determined on a capillary electrothermal melting point apparatus and are uncorrected.

$^1$H NMR spectra were recorded on Varian Unity Inova 300 MHz spectrometer and processed with the MestReC software. All NMR spectra were recorded using $CDCl_3$ as solvent unless otherwise stated and chemical shifts are reported in ppm relative to tetramethylsilane as internal standard. Multiplicities are indicated as s (singlet), d (doublet), dd (doblet of doublets), ddd (doublet of doublet of doublets), dddd (doublet of doublet of doublet of doublets), t (triplet), m (multiplet), and coupling constants (J) are reported in hertz (Hz).

Mass spectra were recorded on a Hewlett-Packard G2000 GC/MS system with HP-5971 gas chromatograph with an electron ionization detector.

Elemental analyses were performed on Perkin-Elmer 2400 series II Analyzer by Microanalytical Laboratory at the Department of Chemistry, Hebrew University of Jerusalem.

Synthetic Preparations of Compounds (3) and (4):

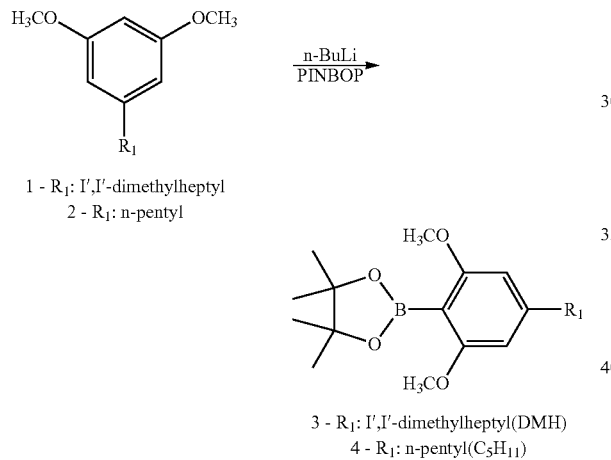

1 - $R_1$: 1′,1′-dimethylheptyl
2 - $R_1$: n-pentyl

3 - $R_1$: 1′,1′-dimethylheptyl(DMH)
4 - $R_1$: n-pentyl($C_5H_{11}$)

2-(2,6-dimethoxy-4-(2-methylheptan-2-yl)phenyl)-4,4,5,5-tetramethyl-1,3,2-dioxaborolane. (3)

To a solution of 4-alkyl resorcinol dimethylether 1 0.132 g (0.5 mmol) in 4 ml of THF n-BuLi 0.34 ml (0.55 mmol, 1.6 M solution in hexane) was added at 0° C. After additional stirring for 1 h at 0° C., the reaction mixture was cooled to −78° C. and a solution of PINBOP 0.15 ml (0.75 mmol) was added all at once. The reaction mixture was allowed to warm up to the room temperature and continued to stir overnight. The reaction worked up with aqueous $NH_4Cl$, extracted with 3 portions of diethyl ether which washed with brine and water. The organic phase was dried over $MgSO_4$ and concentrated in vacuo. The product was obtained as a non-separable mixture of pinacol aryl boronate 3 and 4-alkyl resorcinol dimethylether 1 (in ratio 4:3 according to GC-MS analysis) 0.19 g and was used as it is in Suzuki coupling reaction. The $^1$H NMR (300 MHz, $CDCl_3$) δ ppm 6.41 (s, 2H), 3.76 (s, 6H), 1.51-1.58 (m, 2H), 1.37 (s, 6H), 1.25 (s, 6H), 1.24 (s, 6H), 1.13-1.21 (m, 8H), 0.84 (t, J=6.87 Hz, 3H). Exact mass calculated for $C_{27}H_{34}O_3$ m/e 390.29. found 390.80.

2-(2,6-dimethoxy-4-pentylphenyl)-4,4,5,5-tetramethyl-1,3,2-dioxaborolane (4)

The title compound was prepared by the general procedure described for compound 3, using 4-alkyl resorcinol dimethylether 2 0.104 g (0.5 mmol) in 4 ml of THF, n-BuLi 0.34 ml (0.55 mmol, 1.6 M solution in hexane) and PINBOP 0.15 ml (0.75 mmol). The product was obtained as a non-separable mixture 0.165 g of pinacol aryl boronate 4 and 4-alkyl resorcinol dimethylether 2 (in ratio 4:3 according to GC-MS analysis) and was used as it is in Suzuki coupling reaction. $^1$H NMR (300 MHz, $CDCl_3$) δ ppm 6.28 (s, 2H), 3.76 (s, 6H), 2.55 (t, J=7.53 Hz, 2H), 1.55-1.63 (m, 2H), 1.27 (s, 6H), 1.26 (s, 6H), 1.24 (m, 4H), 0.87 (m, 3H). Exact mass calculated for $C_{27}H_{34}O_3$ m/e 334.23. found 334.62.

Synthetic Preparations of Compound (7):

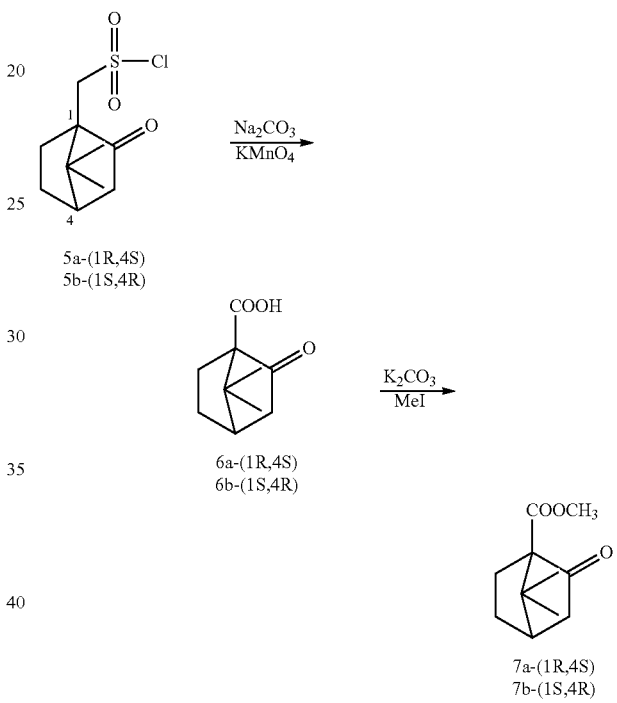

5a-(1R,4S)
5b-(1S,4R)

6a-(1R,4S)
6b-(1S,4R)

7a-(1R,4S)
7b-(1S,4R)

(1R,4S)-methyl-7,7-dimethyl-2-oxobicyclo[2.2.1]heptane-1-carboxylate (7a)

To a mixture of ketopinic acid 6a 0.182 g (1 mmol) and $K_2CO_3$ 1.1 g (8 mmol) stirred in DMF 10 ml was added MeI 0.125 ml (0.284 g, 2 mmol). The reaction mixture was allowed to stir for 18 hrs at ambient temperature. The reaction mixture was dissolved in water 80 ml and extracted with 3×30 ml portions of diethyl ether. The organic phase was washed with $NaHCO_3$ saturated solution, dried over $MgSO_4$ and concentrated in vacuo to give yellow oil 0.184 g (94%). $^1$H NMR (300 MHz, $CDCl_3$) δ ppm 3.75 (s, 3H), 2.53 (ddd, J=18.29, 3.7 Hz, 1H), 2.36 (ddd, J=14.99, 11.82, 3.99 Hz, 1H), 2.10 (t, J=4.4 Hz, 1H), 2.02 (m, 1H), 1.92-1.98 (d, J=18.40 Hz, 1H), 1.79 (ddd, J=14.16, 9.35, 4.95 Hz, 1H), 1.41 (ddd, J=12.65, 9.49, 4.26 Hz, 1H), 1.15 (s, 3H), 1.07 (s, 3H). Exact mass calculated for $C_{11}H_{16}O_3$ m/e 196.11. found 196.22.

(1S,4R)-methyl-7,7-dimethyl-2-oxobicyclo[2.2.1]heptane-1-carboxylate (7b)

The title compound was prepared from 6b by the general procedure described for compound 7a. Yellow oil (96%). $^1$H NMR (300 MHz, CDCl$_3$) δ ppm 3.75 (s, 3H), 2.53 (ddd, J=18.29, 3.7 Hz, 1H), 2.36 (ddd, J=14.99, 11.82, 3.99 Hz, 1H), 2.10 (t, J=4.4 Hz, 1H), 2.02 (m, 1H), 1.92-1.98 (d, J=18.40 Hz, 1H), 1.79 (ddd, J=14.16, 9.35, 4.95 Hz, 1H), 1.41 (ddd, J=12.65, 9.49, 4.26 Hz, 1H), 1.15 (s, 3H), 1.07 (s, 3H). Exact mass calculated for C$_{11}$H$_{16}$O$_3$ m/e 196.11. found 196.22.

Synthetic Preparations of Compounds (9) and (10):

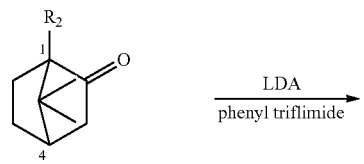

7a-(1R,4S); R$_2$: COOCH$_3$
7b-(1S,4R); R$_2$: COOCH$_3$
8a-(1R,4R); R$_2$: CH$_3$
8b-(1S,4S); R$_2$: CH$_3$

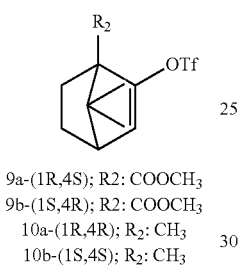

9a-(1R,4S); R$_2$: COOCH$_3$
9b-(1S,4R); R$_2$: COOCH$_3$
10a-(1R,4R); R$_2$: CH$_3$
10b-(1S,4S); R$_2$: CH$_3$ (1R,4S)-methyl-7,7-dimethyl-2-(trifluoromethylsul-fonyloxy)bicyclo[2.2.1]hept-2-ene-1-carboxylate (9a)

Precooled (0° C.) solution of methyl ester 7a 0.06 g (0.3 mmol) in 1.5 ml THF was added to a solution of LDA 0.17 ml (0.34 mmol, 2M solution) in 2 ml THF at −78° C. and resultant solution was allowed to stir for 2 hrs. A solution of phenyl triflimide 0.115 g (0.32 mmol) in 2 ml of THF was added, and the reaction was stirred at 0° C. for 3 hrs and was allowed to stir for additional 15 hrs at room temperature. After the solvent removal at the rotary evaporator, the resultant, yellow oil was purified by silica gel chromatography (petroleum ether/ether) to give brownish oil 0.07 g (71%). $^1$H NMR (300 MHz, CDCl$_3$) δ ppm 5.81 (d, J=3.74, 1H), 3.77 (s, 3H), 2.51 (t, J=3.67 Hz, 1H), 2.39 (ddd, J=3.71, 8.76, 12.47 Hz, 1H), 2.03-2.13 (m, 1H), 1.65 (ddd, J=3.68, 9.18, 12.65 Hz, 1H), 1.24 (ddd, J=3.72, 9.18, 12.64 Hz, 1H), 1.11 (s, 3H), 0.97 (s, 3H). Exact mass calculated for C$_{12}$H$_{15}$F$_3$O$_5$S m/e 328.06. found 328.44.

(1S,4R)-methyl-7,7-dimethyl-2-(trifluoromethylsul-fonyloxy)bicyclo[2.2.1]hept-2-ene-1-carboxylate (9b)

The title compound was prepared from 7b by the general procedure described for compound 9a. Brownish oil (68%). $^1$H NMR (300 MHz, CDCl$_3$) δ ppm 5.81 (d, J=3.74, 1H), 3.77 (s, 3H), 2.51 (dd, J=3.67, 3.67 Hz, 1H), 2.39 (ddd, J=3.71, 8.76, 12.47 Hz, 1H), 2.03-2.13 (m, 1H), 1.65 (ddd, J=3.68, 9.18, 12.65 Hz, 1H), 1.24 (ddd, J=3.72, 9.18, 12.64 Hz, 1H), 1.11 (s, 3H), 0.97 (s, 3H). Exact mass calculated for C$_{12}$H$_{15}$F$_3$O$_5$S m/e 328.06. found 328.44.

Synthetic Preparations of Compounds (11), (12) and (13):

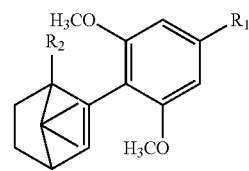

9a-(1R,4S); R2: COOCH$_3$
9b-(1S,4R); R2: COOCH$_3$
10a-(1R,4R); R2: CH$_3$
10b-(1S,4S); R2: CH$_3$

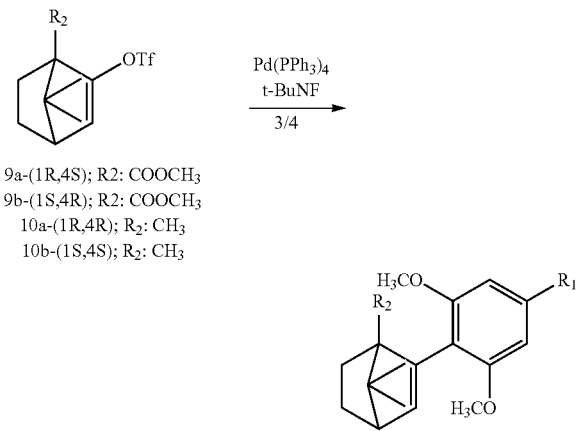

11a-(1R,4S); R$_1$: DMH; R$_2$: COOCH$_3$
11b-(1S,4R); R$_1$: DMH; R$_2$: COOCH$_3$
12a-(1R,4R); R$_1$: DMH; R$_2$: CH$_3$
12b-(1S,4S); R$_1$: DMH; R$_2$: CH$_3$
13a-(1R,4S); R$_1$: C$_5$H$_{11}$; R$_2$: COOCH$_3$
13b-(1S,4R); R$_1$: C$_5$H$_{11}$; R$_2$: COOCH$_3$ (1R,4S)-methyl-2-(2,6-dimethoxy-4-(2-methyloctan-2-yl)phenyl)-7,7-dimethylbicyclo[2.2.1]hept-2-ene-1-carboxylate (11a)

A pinacol arylboronate 3 (mixed with 4-alkyl resorcinol dimethylether 1) 0.474 g, enol triflate 9a 0.328 g (1.00 mmol), Pd(PPh$_3$)$_4$ 0.07 g (0.006 mmol) and t-BuNF 1.5 ml (1.5 mmol, 1M solution in THF) in THF 15 ml were refluxed for 15 hrs. The reaction mixture was filtered through Celite and the filtrate was concentrated in vacuo. Further purification by silica gel column chromatography (petroleum ether/ether) afforded a desired product as pale yellow oil 0.288 g (65%). $^1$H NMR (300 MHz, CDCl$_3$) δ ppm 6.45 (s, 2H), 6.28 (d, J=3.42 Hz, 1H), 3.72 (s, 6H), 3.45 (s, 3H), 2.43 (m, 2H), 1.80-2.03 (m, 1H), 1.53-1.58 (m, 2H), 1.26 (s, 6H), 1.13-1.22 (m, 7H), 1.11 (s, 3H), 0.98-1.08 (m, 3H), 0.97 (s, 3H), 0.84 (t, J=6.79 Hz, 3H). Exact mass calculated for C$_{28}$H$_{42}$O$_4$ m/e 442.31. found 442.92. Anal. calcd. for C$_{28}$H$_{42}$O$_4$: C, 75.98; H, 9.56. Found: C, 76.14; H, 9.65.

(1S,4R)-methyl-2-(2,6-dimethoxy-4-(2-methyloctan-2-yl)phenyl)-7,7-dimethylbicyclo[2.2.1]hept-2-ene-1-carboxylate (11b, HU-912)

The title compound was prepared from 9b by the general procedure described for compound 11a. Yellowish oil (69%). $^1$H NMR (300 MHz, CDCl$_3$) δ ppm 6.45 (s, 2H), 6.28 (d, J=3.42 Hz, 1H), 3.72 (s, 6H), 3.45 (s, 3H), 2.43 (m, 2H), 1.80-2.03 (m, 1H), 1.53-1.58 (m, 2H), 1.26 (s, 6H), 1.13-1.22 (m, 7H), 1.11 (s, 3H), 0.98-1.08 (m, 3H), 0.97 (s, 3H), 0.84 (t, J=6.79 Hz, 3H). Exact mass calculated for C$_{28}$H$_{42}$O$_4$ m/e 442.31. found 442.91. Anal. calcd. for C$_{28}$H$_{42}$O$_4$: C, 75.98; H, 9.56. Found: C, 75.58; H, 9.70.

(1R,4S)-methyl-2-(2,6-dimethoxy-4-pentylphenyl)-7,7-dimethylbicyclo[2.2.1]hept-2-ene-1-carboxylate (13a, HU-971)

The title compound was prepared by the general procedure described for compound 11a (HU-911), using pinacol arylboronate 4 (mixed with 2) 0.244 g, enol triflate 9a 0.2 g (0.61 mmol), Pd(PPh$_3$)$_4$ 0.042 g (0.037 mmol) and t-BuNF 0.91 ml (0.91 mmol, 1M solution in THF) to give colorless oil 170 mg (72%). $^1$H NMR (300 MHz, CDCl$_3$) δ ppm 6.33 (s, 2H), 6.26 (d, J=3.42 Hz, 1H), 3.71 (s, 6H), 3.47 (s, 3H), 2.55 (t, J=7.70 Hz, 2H), 2.38-2.46 (m, 2H), 1.81-2.03 (m, 2H), 1.56-1.66 (m, 2H), 1.30-1.35 (m, 4H), 1.12 (s, 3H, syn), 1.07-1.16 (m, 1H), 0.97 (s, 3H, anti), 0.90 (t, J=6.84 Hz, 3H). Exact mass calculated for C$_{24}$H$_{34}$O$_4$ by the general procedure described for compo$_4$O$_4$: C, 74.58; H, 8.87. Found: C, 74.61; H, 9.04.

(1S,4R)-methyl-2-(2,6-dimethoxy-4-pentylphenyl)-7,7-dimethylbicyclo[2.2.1]hept-2-ene-1-carboxylate (13b, HU-972)

The title compound was prepared from 9b by the general procedure described for compound 13a (HU-971). Colorless oil (69%). $^1$H NMR (300 MHz, CDCl$_3$) δ ppm 6.33 (s, 2H), 6.26 (d, J=3.42 Hz, 1H), 3.71 (s, 6H), 3.47 (s, 3H), 2.55 (t, J=7.70 Hz, 2H), 2.38-2.46 (m, 2H), 1.81-2.03 (m, 2H), 1.56-1.66 (m, 2H), 1.30-1.35 (m, 4H), 1.12 (s, 3H, syn), 1.07-1.16 (m, 1H), 0.97 (s, 3H, anti), 0.90 (t, J=6.84 Hz, 3H). Exact mass calculated for C$_{24}$H$_{34}$O$_4$ m/e 386.25. found 386.67. Anal. calcd. for C$_{24}$H$_{34}$O$_4$: C, 74.58; H, 8.87. Found: C, 74.31; H, 8.90.

(1R,4R)-2-(2,6-dimethoxy-4-(2-methyloctan-2-yl)phenyl)-1,7,7-trimethylbicyclo[2.2.1]hept-2-ene (12a, HU-907)

The title compound was prepared by the general procedure described for compound 11a, using pinacol arylboronate 3 (mixed with 1) 0.755 g, camphor enol triflate 10a 0.5 g (1.76 mmol), Pd(PPh$_3$)$_4$ 0.122 g (0.011 mmol) and t-BuNF 2.64 ml (2.64 mmol, 1M solution in THF) to give yellowish oil 0.525 g (75%), which solidified upon standing at −20° C. to give a white solid. mp 34-36° C.; $^1$H NMR (300 MHz, CDCl$_3$) δ ppm 6.50 (s, 2H), 5.87 (d, J=3.27 Hz, 1H), 3.74 (s, 6H), 2.37 (t, J=3.46, 1H), 1.88 (m, 1H), 1.65 (m, 1H), 1.61 (m, 2H), 1.55 (m, 1H), 1.30 (s, 6H), 1.15 (m, 1H), 1.19-1.26 (m, 6H), 1.07-1.18 (m, 2H), 1.05 (s, 3H), 0.86 (t, J=6.71 Hz, 3H), 0.83 (s, 3H), 0.82 (s, 3H). Exact mass calculated for C$_{27}$H$_{42}$O$_2$ m/e 398.32. found 398.79. Anal. calcd. for C$_{27}$H$_{42}$O$_2$: C, 81.35; H, 10.62. Found: C, 81.08; H, 10.69.

(1S,4S)-2-(2,6-dimethoxy-4-(2-methyloctan-2-yl)phenyl)-1,7,7-trimethylbicyclo[2.2.1]hept-2-ene (12b, HU-908)

The title compound was prepared from 10b by the general procedure described for compound 12a (HU-907). White solid (81%). mp 35-37° C.; $^1$H NMR (300 MHz, CDCl$_3$) δ ppm 6.50 (s, 2H), 5.87 (d, J=3.27 Hz, 1H), 3.74 (s, 6H), 2.37 (t, J=3.46, 1H), 1.88 (m, 1H), 1.65 (m, 1H), 1.61 (m, 2H), 1.55 (m, 1H), 1.30 (s, 6H), 1.15 (m, 1H), 1.19-1.26 (m, 6H), 1.07-1.18 (m, 2H), 1.05 (s, 3H), 0.86 (t, J=6.71 Hz, 3H), 0.83 (s, 3H), 0.82 (s, 3H). Exact mass calculated for C$_{27}$H$_{42}$O$_2$ m/e 398.32. found 398.79. Anal. calcd. for C$_{27}$H$_{42}$O$_2$: C, 81.35; H, 10.62. Found: C, 81.47; H, 10.85.

Synthetic Preparations of Compounds (14) and (15):

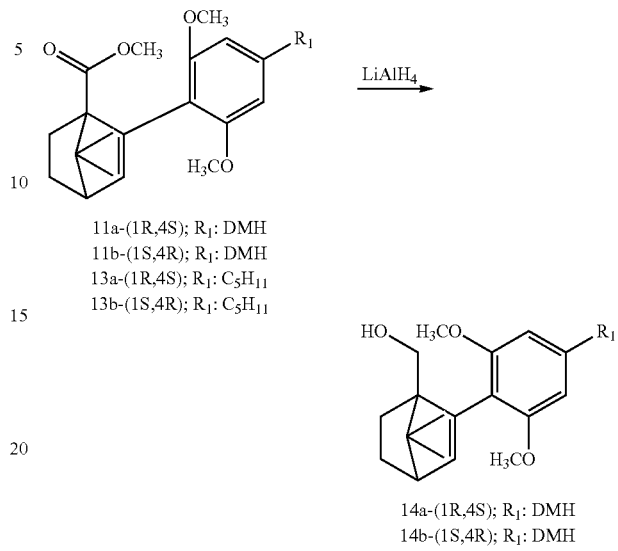

11a-(1R,4S); R$_1$: DMH
11b-(1S,4R); R$_1$: DMH
13a-(1R,4S); R$_1$: C$_5$H$_{11}$
13b-(1S,4R); R$_1$: C$_5$H$_{11}$ 14a-(1R,4S); R$_1$: DMH
14b-(1S,4R); R$_1$: DMH
15a-(1R,4S); R$_1$: C$_5$H$_{11}$
15b-(1S,4R); R$_1$: C$_5$H$_{11}$

(1R,4S)-(2-(2,6-dimethoxy-4-(2-methyloctan-2-yl)phenyl)-7,7-dimethylbicyclo[2.2.1]hept-2-en-1-yl)methanol (14a, HU-909)

Solution of methyl ester 11a 0.790 g (1.79 mmol) in THF 20 ml was cooled to 0° C. After addition of LiAlH$_4$ 3.58 ml (3.58 mmol, 1M solution in diethyl ether) the reaction was allowed to warm up to ambient temperature and stirred for 18 hrs. The reaction worked up with a small amount of saturated MgSO$_4$ solution and extracted with ethyl acetate. The organic phase was washed with brine and water, dried over MgSO$_4$ and concentrated in vacuo. The product was purified by silica gel column chromatography (petroleum ether/ether) to give oil 0.460 g (62%), which solidified upon standing at −20° C. to give a yellow solid. mp 49-51° C.; $^1$H NMR (300 MHz, CDCl$_3$) δ ppm 6.52 (s, 2H), 5.90 (d, J=3.24 Hz, 1H), 3.75 (s, 6H), 3.65 (m, 2H), 2.35 (t, J=3.39, 1H), 2.25 (dd, J=7.29, J=5.01, 1H), 1.93 (m, 1H), 1.53-1.59 (m, 5H), 1.27 (s, 6H), 1.21 (s, 3H), 1.0-1.19 (m, 7H), 0.94 (s, 3H), 0.85 (t, J=6.71 Hz, 3H). Exact mass calculated for C$_{27}$H$_{42}$O$_3$ m/e 414.31. found 414.87. Anal. calcd. for C$_{27}$H$_{42}$O$_3$: C, 78.21; H, 10.21. Found: C, 78.31; H, 10.31.

(1S,4R)-(2-(2,6-dimethoxy-4-(2-methyloctan-2-yl)phenyl)-7,7-dimethylbicyclo[2.2.1]hept-2-en-1-yl)methanol (14b, HU-910)

The title compound was prepared from 11b (HU-912) by the general procedure described for compound 14a (HU-909). White solid (64%). mp 48-50° C.; $^1$H NMR (300 MHz, CDCl$_3$) δ ppm 6.52 (s, 2H), 5.90 (d, J=3.24 Hz, 1H), 3.75 (s, 6H), 3.65 (m, 2H), 2.35 (t, J=3.39, 1H), 2.25 (dd, J=7.29, J=5.01, 1H), 1.93 (m, 1H), 1.53-1.59 (m, 5H), 1.27 (s, 6H), 1.21 (s, 3H), 1.0-1.19 (m, 7H), 0.94 (s, 3H), 0.85 (t, J=6.71 Hz, 3H). Exact mass calculated for C$_{27}$H$_{42}$O$_3$ m/e 414.31. found 414.86. Anal. calcd. for C$_{27}$H$_{42}$O$_3$: C, 78.21; H, 10.21. Found: C, 78.08; H, 10.32.

(1R,4S)-(2-(2,6-dimethoxy-4-pentylphenyl)-7,7-dimethylbicyclo[2.2.1]hept-2-en-1-yl)methanol (15a, HU-969)

The title compound was prepared by the general procedure described for compound 14a (HU-909), using methyl ester 13a (HU-971) 0.1 g (0.259 mmol) in 3 ml of dry THF and LiAlH$_4$ 0.51 ml (0.518 mmol, 1M solution in diethyl ether). The product was purified by silica gel column chromatography (petroleum ether/ether) to give oil 0.086 g (93%), which solidified upon standing at −20° C. to give a white solid. mp 28-29° C.; $^1$H NMR (300 MHz, CDCl$_3$) δ ppm 6.40 (s, 2H), 5.88 (d, J=3.24 Hz, 1H), 3.74 (s, 6H), 3.65 (d, J=2.51 Hz, 2H), 2.58 (t, J=7.70 Hz, 2H), 2.35 (t, J=3.41 Hz, 1H), 1.89-1.98 (m, 1H), 1.54-1.66 (m, 4H), 1.32-1.38 (m, 4H), 1.23 (s, 3H), 1.11-1.19 (m, 1H), 0.94 (s, 3H), 0.92 (t, J=6.84 Hz, 3H). Exact mass calculated for C$_{23}$H$_{34}$O$_3$ m/e 358.25. found 358.67. Anal. calcd. for C$_{23}$H$_{34}$O$_3$: C, 77.05; H, 9.56. Found: C, 77.06; H, 9.72.

(1S,4R)-(2-(2,6-dimethoxy-4-pentylphenyl)-7,7-dimethylbicyclo[2.2.1]hept-2-en-1-yl)methanol (15b, HU-970)

The title compound was prepared from 10b by the general procedure described for compound 13b (HU-972). Oil (83%), which solidified upon standing at −20° C. mp 26-27° C.; $^1$H NMR (300 MHz, CDCl$_3$) δ ppm 6.40 (s, 2H), 5.88 (d, J=3.24 Hz, 1H), 3.74 (s, 6H), 3.65 (d, J=2.51 Hz, 2H), 2.58 (t, J=7.70 Hz, 2H), 2.35 (t, J=3.41 Hz, 1H), 1.89-1.98 (m, 1H), 1.54-1.66 (m, 4H), 1.32-1.38 (m, 4H), 1.23 (s, 3H), 1.11-1.19 (m, 1H), 0.94 (s, 3H), 0.92 (t, J=6.84 Hz, 3H). Exact mass calculated for C$_{23}$H$_{34}$O$_3$ m/e 358.25. found 358.71. Anal. calcd. for C$_{23}$H$_{34}$O$_3$: C, 77.05; H, 9.56. Found: C, 76.25; H, 9.55.

Synthetic Preparations of Compounds (16) and (17):

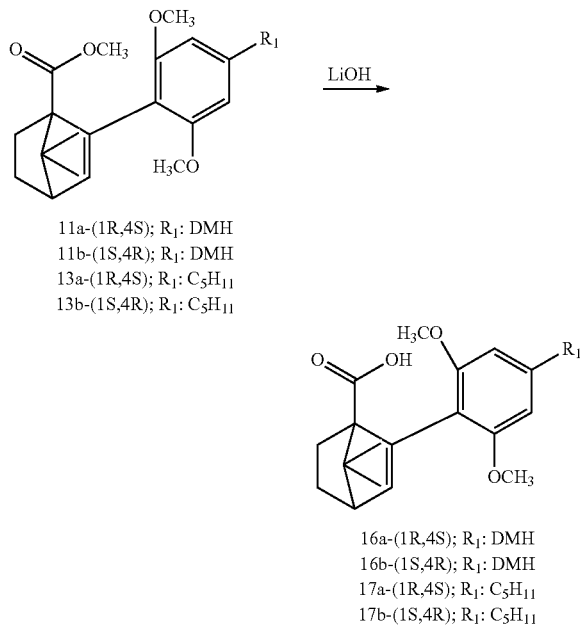

11a-(1R,4S); R$_1$: DMH
11b-(1S,4R); R$_1$: DMH
13a-(1R,4S); R$_1$: C$_5$H$_{11}$
13b-(1S,4R); R$_1$: C$_5$H$_{11}$ 16a-(1R,4S); R$_1$: DMH
16b-(1S,4R); R$_1$: DMH
17a-(1R,4S); R$_1$: C$_5$H$_{11}$
17b-(1S,4R); R$_1$: C$_5$H$_{11}$

(1R,4S)-2-(2,6-dimethoxy-4-(2-methyloctan-2-yl)phenyl)-7,7-dimethylbicyclo[2.2.1]hept-2-ene-1-carboxylic acid (16a, HU-913)

Methyl ester 11a (HU-911) 0.103 g (0.233 mmol) and LiOH 0.111 g (4.66 mmol) in 2 ml of MeOH/H$_2$O 3:1 were heated at 200° C. over 48 hrs in a screwed vial under air atmosphere. Water was added to the reaction mixture and extracted several times with ether. Organic phases were collected, dried over MgSO$_4$ and concentrated in vacuo. The product was purified by preparative TLC (hexane/ethyl acetate) to give yellow solid 0.026 g (26%). mp 101-102° C.; $^1$H NMR (300 MHz, CDCl$_3$) δ ppm 6.46 (s, 2H), 6.32 (d, J=3.40 Hz, 1H), 3.71 (s, 6H), 2.46 (t, J=3.44 Hz, 1H), 2.38-2.44 (m, 1H), 1.80-2.03 (m, 1H), 1.53-1.58 (m, 2H), 1.26 (s, 6H), 1.16-1.24 (m, 7H), 1.14 (s, 3H), 1.03-1.12 (m, 3H), 1.00 (s, 3H), 0.85 (t, J=6.74 Hz, 3H). Exact mass calculated for C$_{28}$H$_{42}$O$_4$ m/e 428.29. found 428.98. Anal. calcd. for C$_{28}$H$_{42}$O$_4$: C, 75.66; H, 9.41. Found: C, 75.50; H, 9.48.

(1S,4R)-2-(2,6-dimethoxy-4-(2-methyloctan-2-yl)phenyl)-7,7-dimethylbicyclo[2.2.1]hept-2-ene-1-carboxylic acid (16b, HU-914)

The title compound was prepared from 11b (HU-912) by the general procedure described for compound 16a (HU-913). Yellow solid (25%). mp 100-101° C.; $^1$H NMR (300 MHz, CDCl$_3$) δ ppm 6.46 (s, 2H), 6.32 (d, J=3.40 Hz, 1H), 3.71 (s, 6H), 2.46 (t, J=3.44 Hz, 1H), 2.38-2.44 (m, 1H), 1.80-2.03 (m, 1H), 1.53-1.58 (m, 2H), 1.26 (s, 6H), 1.16-1.24 (m, 7H), 1.14 (s, 3H), 1.03-1.12 (m, 3H), 1.00 (s, 3H), 0.85 (t, J=6.74 Hz, 3H). Exact mass calculated for C$_{28}$H$_{42}$O$_4$ m/e 428.29. found 428.98. Anal. calcd. for C$_{28}$H$_{42}$O$_4$: C, 75.66; H, 9.41. Found: C, 74.81; H, 9.40.

(1R,4S)-2-(2,6-dimethoxy-4-pentylphenyl)-7,7-dimethylbicyclo[2.2.1]hept-2-ene-1-carboxylic acid (17a, HU-973)

The title compound was prepared by the general procedure described for compound 16a (HU-913), using methyl ester 13a (HU-971) 0.075 g (0.194 mmol) and LiOH 0.093 g (3.89 mmol) in 1.5 ml of MeOH/H$_2$O 3:1. The product was purified by preparative TLC (hexane/ethyl acetate) to give yellowish solid 0.010 g (14%). mp 85-87° C.; $^1$H NMR (300 MHz, CDCl$_3$) δ ppm 6.33 (s, 2H), 6.28 (d, J=3.39 Hz, 1H), 3.69 (s, 6H), 2.55 (t, J=7.80 Hz, 2H), 2.45 (t, J=3.48 Hz, 1H), 2.36-2.44 (m, 1H), 1.82-2.03 (m, 2H), 1.55-1.65 (m, 2H), 1.30-1.35 (m, 4H), 1.14 (s, 3H), 1.06-1.12 (m, 1H), 1.00 (s, 3H), 0.90 (t, J=6.84 Hz, 3H). Exact mass calculated for C$_{23}$H$_{32}$O$_4$ m/e 372.23. found 372.92. Anal. calcd. for C$_{23}$H$_{32}$O$_4$: C, 74.16; H, 8.66. Found: C, 73.91; H, 8.80.

(1S,4R)-2-(2,6-dimethoxy-4-pentylphenyl)-7,7-dimethylbicyclo[2.2.1]hept-2-ene-1-carboxylic acid (17b, HU-974)

The title compound was prepared from 13b (HU-972) by the general procedure described for compound 17a (HU-973). Yellowish solid (21%). mp 84-86° C.; $^1$H NMR (300 MHz, CDCl$_3$) δ ppm 6.33 (s, 2H), 6.28 (d, J=3.39 Hz, 1H), 3.69 (s, 6H), 2.55 (t, J=7.80 Hz, 2H), 2.45 (t, J=3.48 Hz, 1H), 2.36-2.44 (m, 1H), 1.82-2.03 (m, 2H), 1.55-1.65 (m, 2H), 1.30-1.35 (m, 4H), 1.14 (s, 3H), 1.06-1.12 (m, 1H), 1.00 (s, 3H), 0.90 (t, J=6.84 Hz, 3H). Exact mass calculated for C$_{23}$H$_{32}$O$_4$ m/e 372.23. found 372.92. Anal. calcd. for C$_{23}$H$_{32}$O$_4$: C, 74.16; H, 8.66. Found: C, 73.60; H, 8.70.

Synthetic Preparations of Compound (19):

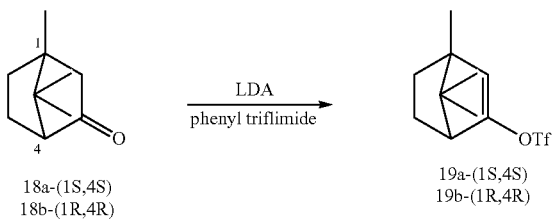 [SMILES: CC12CCC(C(=O)C1)C2(C)C ; CC12C=C(OS(=O)(=O)C(F)(F)F)C(CC1)C2(C)C]

18a-(1S,4S)
18b-(1R,4R)

19a-(1S,4S)
19b-(1R,4R)

(1S,4S)-4,7,7-trimethylbicyclo[2.2.1]hept-2-en-2-yl trifluoromethanesulfonate (19a)

The title compound was prepared by the general procedure described for compound 9a, using ketone 18a 0.375 g (2.35 mmol), LDA 1.29 ml (2.58 mmol, 2M solution) and phenyl triflimide 0.943 g (2.64 mmol). The product was purified by silica gel column chromatography (petroleum ether/ether) to give oil 0.514 g (77%). $^1$H NMR (300 MHz, CDCl$_3$) δ ppm 5.37 (d, J=1.04 Hz, 1H), 2.45 (d, J=3.48 Hz, 1H), 1.93 (dddd, J=3.43, 3.43, 7.85, 11.61 Hz, 1H), 1.70 (ddd, J=3.12, 8.52, 11.84 Hz, 1H), 1.19-1.38 (m, 2H), 1.08 (s, 3H), 0.97 (s, 3H), 0.78 (s, 3H). Exact mass calculated for C$_{11}$H$_{15}$F$_3$O$_3$S, 284.07. found, 284.77.

(1R,4R)-4,7,7-trimethylbicyclo[2.2.1]hept-2-en-2-yl trifluoromethanesulfonate (19b)

The title compound was prepared from 18b by the general procedure described for compound 19a. Brownish oil (73%). $^1$H NMR (300 MHz, CDCl$_3$) δ ppm 5.37 (d, J=1.04 Hz, 1H), 2.45 (d, J=3.48 Hz, 1H), 1.93 (dddd, J=3.43, 3.43, 7.85, 11.61 Hz, 1H), 1.70 (ddd, J=3.12, 8.52, 11.84 Hz, 1H), 1.19-1.38 (m, 2H), 1.08 (s, 3H), 0.97 (s, 3H), 0.78 (s, 3H). Exact mass calculated for C$_{11}$H$_{15}$F$_3$O$_3$S, 284.07. found, 284.77.

Synthetic Preparations of Compound (20):

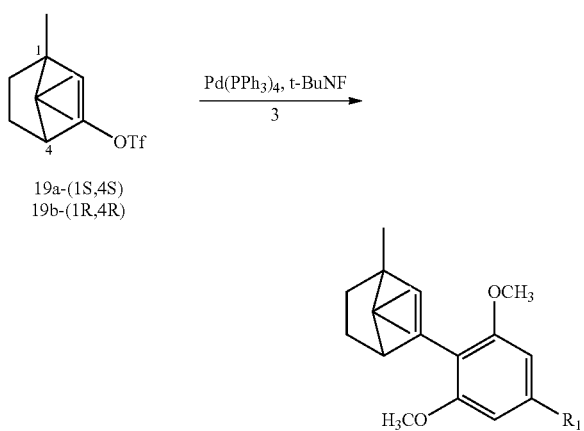

19a-(1S,4S)
19b-(1R,4R)

20a-(1S,4S); R1: DMH
20b-(1R,4R); R1: DMH (1S,4S)-3-(2,6-dimethoxy-4-(2-methyloctan-2-yl)phenyl)-1,7,7-trimethylbicyclo[2.2.1]hept-2-ene (20a, HU-917)

The title compound was prepared by the general procedure described for compound 11a (HU-911), using pinacol aryl-boronate 3 (mixed with 4-alkyl resorcinol dimethylether 1) 0.755 g, enol triflate 19a 0.17 g (0.598 mmol), Pd(PPh$_3$)$_4$ 0.041 g (0.036 mmol) and t-BuNF 0.9 ml (0.9 mmol, 1M solution in THF). The product was purified by silica gel column chromatography (petroleum ether/ether) to give oil 0.185 g (78%), which solidified upon standing at −20° C. mp 33-34° C.; $^1$H NMR (300 MHz, CDCl$_3$) δ ppm 6.50 (s, 2H), 5.79 (d, J=3.00 Hz, 1H), 3.76 (s, 6H), 2.60 (d, J=3.51, 1H), 1.81 (m, 1H), 1.64 (m, 1H), 1.60 (m, 1H), 1.55 (m, 2H), 1.31 (m, 1H), 1.28 (s, 6H), 1.17-1.25 (m, 8H), 1.08 (s, 3H), 0.99 (s, 3H), 0.86 (t, J=6.69 Hz, 3H), 0.81 (s, 3H). Exact mass calculated for C$_{27}$H$_{42}$O$_2$ m/e 398.32. found 398.82. Anal. calcd. for C$_{27}$H$_{42}$O$_2$: C, 81.35; H, 10.62. Found: C, 81.50; H, 10.71.

(1R,4R)-3-(2,6-dimethoxy-4-(2-methyloctan-2-yl)phenyl)-1,7,7-trimethylbicyclo[2.2.1]hept-2-ene (20b, HU-918)

The title compound was prepared from 19b by the general procedure described for compound 20a (HU-917). Yellowish solid (77%). mp 32-33° C.; $^1$H NMR (300 MHz, CDCl$_3$) δ ppm 6.50 (s, 2H), 5.79 (d, J=3.00 Hz, 1H), 3.76 (s, 6H), 2.60 (d, J=3.51, 1H), 1.81 (m, 1H), 1.64 (m, 1H), 1.60 (m, 1H), 1.55 (m, 2H), 1.31 (m, 1H), 1.28 (s, 6H), 1.17-1.25 (m, 8H), 1.08 (s, 3H), 0.99 (s, 3H), 0.86 (t, J=6.69 Hz, 3H), 0.81 (s, 3H). Exact mass calculated for C$_{27}$H$_{42}$O$_2$ m/e 398.32. found 398.84. Anal. calcd. for C$_{27}$H$_{42}$O$_2$: C, 81.35; H, 10.62. Found: C, 81.56; H, 10.85.

Synthetic Preparations of Compounds (22, HU-936) and (23, HU-926):

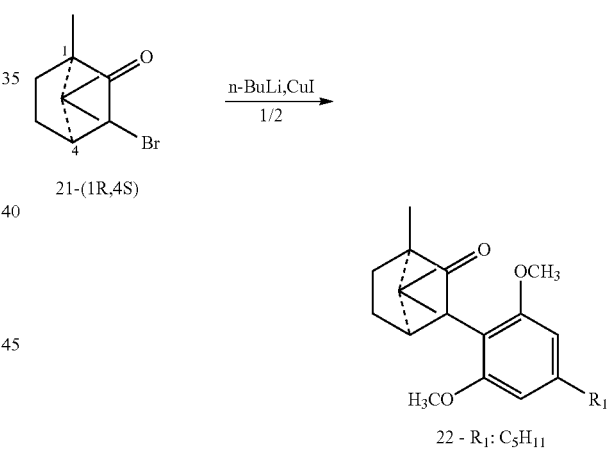

21-(1R,4S)

22 - R$_1$: C$_5$H$_{11}$
23 - R$_1$: DMH (1R,4R)-3-(2,6-dimethoxy-4-pentylphenyl)-1,7,7-trimethylbicyclo[2.2.1]heptan-2-one (22, HU-936)

n-BuLi 0.6 ml (0.96 mmol, 1.6 M in hexanes) was added to a precooled (0° C.) solution of 2 0.2 g (0.96 mmol) in 3 ml of diethyl ether. The resulting solution was allowed to stir for 2.5 hrs at room temperature. The solution was then cooled back to 0° C. and transferred dropwise via cannula to a suspension of CuI 0.092 g (0.48 mmol) in 2 ml of diethyl ether at 0° C. The resulting solution was allowed to stir for 30 min and 5 ml of anhydrous DMSO was added. Then the solution of 3-bromocamphor 21 0.086 g (0.37 mmol) in 1 ml of diethyl ether and 1 ml of DMSO at 0° C. was added dropwise via septum. The reaction was then allowed to warm to room temperature and stirred over 15 hrs. The reaction was quenched by the addition of 5 ml of saturated aqueous $NH_4Cl$. The water phase was extracted three times with diethyl ether. The combined organic layers were washed three times with brine, dried over $MgSO_4$, and the solvent was removed in vacuo. Further purification by silica gel column chromatography (petroleum ether/ether) afforded white crystals of 22 (HU-936) 0.093 g (70%). mp 62° C.; $^1$H NMR (300 MHz, $CDCl_3$) δ ppm 6.37 (s, 2H), 3.89 (d, J=4.23 Hz, 1H), 3.72 (s, 6H), 2.55 (t, J=7.87 Hz, 2H), 2.19 (t, J=4.11 Hz, 1H), 1.71-1.76 (m, 2H), 1.63 (m, 1H), 1.59 (m, 2H), 1.37 (m, 1H), 1.33-1.36 (m, 4H), 1.02 (s, 3H), 1.002 (s, 3H), 0.97 (s, 3H), 0.91 (t, J=6.93 Hz, 3H). Exact mass calculated for $C_{23}H_{34}O_3$ m/e 358.25. found 358.67. Anal. calcd. for $C_{23}H_{34}O_3$: C, 77.05; H, 9.56. Found: C, 77.20; H, 9.63.

(1R,4R)-3-(2,6-dimethoxy-4-(2-methyloctan-2-yl)phenyl)-1,7,7-trimethylbicyclo[2.2.1]heptan-2-one (23, HU-926)

The title compound was prepared by the general procedure described for compound 22 (HU-936), using 1 0.23 g (0.87 mmol), n-BuLi 0.54 ml (0.87 mmol, 1.6 M in hexanes), CuI 0.083 g (0.44 mmol), 3-bromocamphor 21 0.069 g (0.3 mmol). Further purification by silica gel column chromatography (petroleum ether/ether) afforded white crystals of 23 (HU-926) 0.081 g (65%). mp 64-65° C.; $^1$H NMR (300 MHz, $CDCl_3$) δ ppm 6.49 (s, 2H), 3.89 (d, J=4.23 Hz, 1H), 3.72 (s, 6H), 2.19 (t, J=4.11 Hz, 1H), 1.71-1.76 (m, 1H), 1.53-1.68 (m, 4H), 1.30-1.42 (m, 1H), 1.26 (s, 6H), 1.15-1.24 (m, 8H), 1.01 (s, 3H), 1.00 (s, 3H), 0.97 (s, 3H), 0.85 (t, J=6.73 Hz, 3H). Exact mass calculated for $C_{27}H_{42}O_3$ m/e 414.31. found 414.84. Anal. calcd. for $C_{27}H_{42}O_3$: C, 78.21; H, 10.21. Found: C, 78.39; H, 10.27.

Synthetic Preparations of Compounds (24, HU-938) and (25, HU-928):

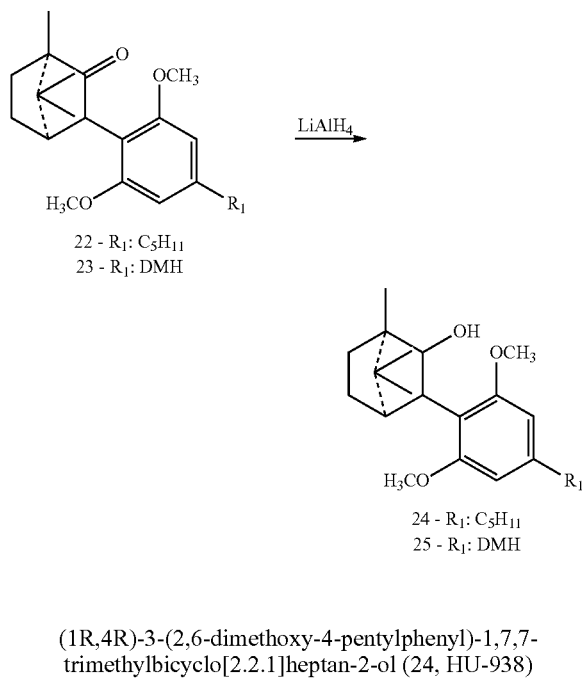

22 - R$_1$: C$_5$H$_{11}$
23 - R$_1$: DMH

24 - R$_1$: C$_5$H$_{11}$
25 - R$_1$: DMH (1R,4R)-3-(2,6-dimethoxy-4-pentylphenyl)-1,7,7-trimethylbicyclo[2.2.1]heptan-2-ol (24, HU-938)

Ketone 22 (HU-936) 0.085 g (0.23 mmol) in 1 ml of diethyl ether was added to a precooled (0° C.) solution of $LiAlH_4$ 0.14 ml (0.14 mmol, 1M solution in diethyl ether) in diethyl ether 2 ml. After stirring under reflux for 1 h the reaction mixture was cooled to 0° C. and quenched by addition of EtOAc.

Water was added to the reaction mixture and it was extracted with 3 portions of diethyl ether, followed by washing with aqueous HCl 10%. The organic phase was dried over $MgSO_4$ and concentrated in vacuo. Further purification by silica gel column chromatography (ether/petroleum ether) afforded white crystals of 24 (HU-938) 0.078 g (92%). mp 58-60° C.; $^1$H NMR (300 MHz, $CDCl_3$) δ ppm 6.44 (s, 2H), 4.52 (d, J=6.96 Hz, J=1.87 Hz, 1H), 4.14-4.17 (m, 2H), 3.82 (s, 6H), 2.56 (t, J=7.70 Hz, 2H), 2.19 (t, J=4.11 Hz, 1H), 1.77-1.89 (m, 2H), 1.63 (m, 1H), 1.46-1.70 (m, 3H), 1.23-1.41 (m, 4H), 1.06 (s, 3H), 0.94 (s, 3H), 0.92 (s, 3H), 0.90 (t, J=6.93 Hz, 3H). Exact mass calculated for $C_{23}H_{36}O_3$ m/e 360.27. found 360.65. Anal. calcd. for $C_{23}H_{36}O_3$: C, 76.62; H, 10.06. Found: C, 76.46; H, 10.11.

(1R,4R)-3-(2,6-dimethoxy-4-(2-methyloctan-2-yl)phenyl)-1,7,7-trimethylbicyclo[2.2.1]heptan-2-ol (25, HU-928)

The title compound was prepared by the general procedure described for compound 24 (HU-938), using ketone 23 (HU-926) 0.238 g (0.57 mmol), $LiAlH_4$ 0.345 ml (0.34 mmol). Further purification by silica gel column chromatography (ether/petroleum ether) afforded white crystals of 25 (HU-928) 0.208 g (88%). mp 96-98° C.; $^1$H NMR (300 MHz, $CDCl_3$) δ ppm 6.55 (s, 2H), 4.58 (dd, J=8.88 Hz, 1H), 4.14-4.17 (m, 2H), 3.82 (s, 6H), 1.78-1.88 (m, 2H), 1.48-1.61 (m, 5H), 1.29-1.33 (m, 1H), 1.27 (s, 6H), 1.16-1.25 (m, 7H), 1.06 (s, 3H), 0.94 (s, 3H), 0.92 (s, 3H), 0.85 (t, J=6.74 Hz, 3H). Exact mass calculated for $C_{27}H_{44}O_3$ m/e 416.33. found 416.90. Anal. calcd. for $C_{27}H_{44}O_3$: C, 77.83; H, 10.64. Found: C, 78.10; H, 10.82.

Example 2

In Vitro Binding to Cannabinoid Receptors

Cell Line Generations and Maintenance

The cDNA clones for human HA-tagged CB1 and CB2 receptors were obtained from the Missouri S&T cDNA Resource Center (www.cdna.org) in cloning vector pcDNA3.1+. The vector containing the human CB2 receptor was transfected directly into CHO-KI cells obtained from ATCC. The HA-tagged human CB1 receptor sequence was subcloned into the pef4-V5-HisA vector with Kpn1 and Pme1 restriction enzymes and subsequently transfected into CHO-K1 cells. Cells were clonally isolated by limited dilution and screened by immunocytochemistry for expression of the HA tag. Clones expressing the HA tag were then screened by RT-PCR to confirm expression of hCB1 and hCB2 receptor mRNA transcripts (data not shown).

Cells were maintained in DMEM/F12 media supplemented with 10% fetal bovine serum (FBS), 100 units/ml penicillin and 100 μg/ml streptomycin and 2 mM L-glutamine. Transfected cell lines were maintained with additional 150 ug/ml zeocin for pEF HA-CB1 transfected cells and 500 ug/ml G-418 for pcDNA HA-CB2 transfected cells (all reagents obtained from Invitrogen).

Membrane Preparation

Cells were grown to confluence and harvested in ice cold phosphate buffered saline with 5 mM EDTA. Cells were spun at 200×g for 10 min and frozen at −80° C. until required. Cell pellets were thawed with cold 0.32 M sucrose and homogenised with a glass homogeniser. The homogenate was spun at 1000×g for 10 min at 4° C. and the supernatant spun in a Sorvall ultracentrifuge for 30 min at 100,000×g. The pellet was then washed in ice cold water and re-spun twice more. The final pellet was resuspended in 50 mM Tris pH 7.5, 0.5 mM EDTA. Protein concentration was determined using the Dc protein assay kit (BioRad, Hercules, Calif., USA).

Membrane Competition Binding Assay

The $K_d$ of CP 55,940 in the isolated CB1 and CB2 receptor expressing membranes was previously determined to be 2.3 nM and 1.5 nM, respectively (see Pertwee, R. G. *Current Medicinal Chemistry* 6 635-664 (1999)). Competition binding assays at 2.5 nM [$^3$H]-CP 55,940 (PerkinElmer) were carried out to determine the $K_i$ values for tested compounds. Membranes (5-10 μg) were incubated with radioligand and a range of concentrations of test compounds in binding buffer (50 mM Tris pH 7.4, 5 mM MgCl$_2$, 1 mM EDTA) with 0.5% (w/v) bovine serum albumin (BSA) (ICP Bio, New Zealand), at 30° C. for 60 min. Stock solutions of putative cannabinoid ligands were prepared in dimethyl sulfoxide to a concentration of 10 mM. Six different final concentrations of compounds were used ranging from 50 μM to 0.1 nM. Non-specific binding was determined in the presence of 1 μM non-radioactive CP 55,940 (Tocris Cookson). Assays were terminated by addition of 2 ml ice cold binding buffer and filtration through GF/C filters (Whatman) pre-soaked in cold binding buffer, followed by two washes in the same buffer.

Radioactivity was determined by incubation of filters with Irgasafe scintillation fluid (PerkinElmer) and scintillation counting in a Wallac Trilux using Microbeta Trilux software. Data was analysed using the Prism 4.02 programme (GraphPad Software, San Deigo, Calif., USA).

cAMP Assays

Cells were seeded at a density of 10,000 cells per well in poly-L-lysine treated 96-well culture plates (BD Biosciences). The following day wells were incubated with 40 μl DMEM/F12 containing 0.5% (w/v) BSA and 0.5 mM 3-isobutyl-1-methylxanthine (Sigma-Aldrich) for 30 minutes prior to 15 min stimulation with 50 μM forskolin (Tocris Cookson) and varying concentrations of indicated compounds at 37° C., 5% $CO_2$. Assays were stopped by removal of media and addition of 100% ice cold ethanol. Plates were then frozen for a minimum of two hours before complete evaporation of ethanol. The well contents were then reconstituted in 50 μl cAMP assay buffer (20 mM HEPES pH 7.5 and 5 mM EDTA). Half of the reconstituted sample was transferred to round bottom 96-well plates (Greiner Bio-One GmbH) with 50 μl 0.01% w/v PKA (cAMP dependent protein kinase (Sigma-Aldrich) in 1 mM Na citrate pH 6.5 with 2 mM dithiothreitol) and 25 μl [$^3$H]-cAMP (at 22 nM in cAMP assay buffer) (GE Healthcare, Life Sciences). This was allowed to equilibrate for 3-18 hours. Following this a charcoal slurry (5% (w/v) activated charcoal and 0.2% (w/v) BSA in cAMP assay buffer) was added to the samples and the plates centrifuged at 3000×g, 4° C. for 5 min. Radioactive counts within the supernatant were then determined as described for competition binding assays.

Membrane [$^{35}$S]GTPγS Binding Assay

Human CB2 expressing CHO-K1 membranes (5 μg per incubation mixture) were diluted in 50 mM Tris-HCl (pH 7.5) and 0.5 mM EDTA and added to HU compounds in a premixed incubation cocktail. Final incubation concentrations were 55 mM Tris-HCl (pH 7.4), 1 mM EDTA, 100 mM NaCl, 5 mM MgCl$_2$, 0.5% BSA, 50 μM GDP, 0.2 nM [$^{35}$S]GTPγS (PerkinElmer) with varied HU compound concentration and 5 μg membrane. Incubations were continued for 60 minutes at 30° C. in a shaking water bath. Assays were terminated by addition of 2 ml ice cold wash buffer (50 mM Tris-HCl, pH 7.5 and 5 mM MgCl$_2$) and filtration through pre-soaked GF/C filters (Whatman), followed by two further washes. adioactivity was determined as described for competition binding assays.

Statistical Analysis

Data was analyzed using the Prism 4.02 programme (GraphPad Software, San Deigo, Calif., USA). IC50 and EC50 values, as determined from sigmoidal curves, were generated from drug concentrations plotted in log scale. While the standard error of the mean (SEM) or standard deviation of these values may be calculated while they are in log form the conversion into molar (linear) values becomes uneven and the error is not able to be expressed as "plus or minus" the calculated values. It is possible to display data as an average, plus or minus the standard error of the mean in log form, however, this is not easily interpreted or compared to other values. It was therefore elected to calculate the 95% confidence interval for the mean value in log form and then convert the lower limit, mean and upper limit into the molar (linear) scale. Although the range depicted in this data format often spans a wide range of concentrations, it is a much more user friendly method of displaying data, the data generated in this chapter is comparable to other similar published results of reputable sources (Pertwee et al., 2000). Two-tailed t-tests for statistical analysis between enantiomeric pairs of compounds were performed for CB2 $K_i$ values. The Pearson value, an indication of linearity, was determined for $K_i$ and IC50 or EC50 results obtained for CB2 receptors in binding, cAMP or GTPγS experiments, respectively. To determine if Emax values were significantly different from HU-308, one-way ANOVA was performed with a Bonferroni post-test of selected pairs.

Results

Efficacy and Affinity of Binding to CB1 and CB2 Receptors.

All data was analyzed using Prism 4.02. For binding data the $K_i$ was determined from $IC_{50}$ values derived from competition binding data fitted with one site competition non-linear regression analysis by Prism 4.02 using the $K_d$ values reported above.

$pIC_{50}$ values were determined from cAMP assays by fitting a sigmoidal concentration response curve using Prism 4.02.

Results shown in Tables 1 and 2 were generated by averaging two independently determined $pIC_{50}$ values. Data shown is $IC_{50}$ (95% confidence interval). $E_{max}$ values were calculated as a percentage of the maximal response detected in parallel cAMP assays with HU-210 (1,1-Dimethylheptyl-11-hydroxy-tetrahydrocannabinol or (6aR)-trans-3-(1,1-Dimethylheptyl)-6a,7,10,10a-tetrahydro-1-hydroxy-6,6-dimethyl-6H-dibenzo[b,d]pyran-9-methan ol) or HU-308 ([(1R,2R,5R)-2-[2,6-dimethoxy-4-(2-methyloctan-2-yl) phenyl]-7,7-dimethyl-4-bicyclo[3.1.1]hept-3-enyl]methanol) for CB1 and CB2 expressing cells respectively. Data are displayed as the mean±SEM.

TABLE 1

Efficacy and affinity of compounds of the invention for the human CB1 and CB2 receptor

| | | Competition Binding Assay | | | | cAMP Assay | | | | | |
| | | CB2 Receptor | | CB1 Receptor | | CB2 Receptor | | | CB1 Receptor | | |
| Compound | HU-number | $K_i$ (nM) | 95% Confidence Interval | $K_i$ (µM) | 95% Confidence Interval | $IC_{50}$ (nM) | 95% Confidence Interval | $E_{max}$ | $IC_{50}$ (µM) | 95% Confidence Interval | $E_{max}$ |
|---|---|---|---|---|---|---|---|---|---|---|---|
| 12a | HU-907 | 2514 | (829, 7630) | NB | — | NB | — | — | NB | — | — |
| 12b | HU-908 | NB | — | NB | — | NB | — | — | NB | — | — |
| 14a | HU-909 | 56.8 | (24.4, 132) | 11.7 | (4.90, 27.9) | 425 | (233, 774) | 95 ± 6% | NB | — | — |
| 14b | HU-910 | 6 | (5.25, 6) | 1.37 | (0.53, 3.56) | 162 | (87.9, 300) | 105 ± 12% | NB | — | — |
| 11a | HU-911 | 84.6§ | (34.9, 204) | NB | — | 385 | (200, 751) | 86 ± 9% | NB | — | — |
| 11b | HU-912 | 77.1§ | (30.0, 199) | >10 µM | — | 239 | (159, 358) | 107 ± 4% | 3.37 | (2.79, 4.06) | 112 ± 8% |
| 16a | HU-913 | 81.5 | (69.6, 95.6) | NB | — | 330 | (195, 557) | 101 ± 11% | NB | — | — |
| 16b | HU-914 | 1500 | (870, 2570) | NB | — | 2290 | (1710, 3050) | 82 ± 7% | NB | — | — |
| 20a | HU-917 | NB | — | NB | — | NB | — | — | NB | — | — |
| 20b | HU-918 | NB | — | NB | — | NB | — | — | NB | — | — |
| 23 | HU-926 | 106 | (55.3, 204) | NB | — | 321 | (203, 511) | 100 ± 13% | NB | — | — |
| 25 | HU-928 | 230 | (36.7, 1450) | NB | — | 925 | (550, 1560) | 101 ± 11% | NB | — | — |
| 22 | HU-936 | 1720 | (827, 3560) | NB | — | NB | — | — | NB | — | — |
| 24 | HU-938 | 7910 | (4610, 13600) | NB | — | NB | — | — | NB | — | — |
| 15a | HU-969 | 6460 | (4800, 7890) | NB | — | NB | — | — | NB | — | — |
| 15b | HU-970 | 1270 | (634, 2530) | NB | — | 1150 | (664, 1980) | 38 ± 2%* | NB | — | — |
| 13a | HU-971 | 704 | (314, 1580) | NB | — | 1530 | (810, 2900) | 31 ± 4%* | NB | — | — |
| 13b | HU-972 | 168 | (115, 247) | NB | — | 313 | (220, 446) | 48 ± 5%* | NB | — | — |
| 17a | HU-973 | 1150 | (596, 2210) | NB | — | 2090 | (1340, 3260) | 40 ± 6%* | NB | — | — |
| 17b | HU-974 | >10 µM | — | NB | — | NB | — | — | NB | — | — |
| | HU-308 | 14 | (8.7, 22.8) | NB | — | 117 | (89.5, 153) | 100 ± 0% | NB | — | — |
| | HU-210 | | | 0.00294 | | | | | | | |

Competition binding assays were performed with either CHO-CB1 or CHO-CB2 cellular membranes and cAMP assays in whole cells expressing the indicated receptor. Binding ($K_i$) and potency (EC50) data is presented as the mean with 95% confidence intervals in parentheses. cAMP derived efficacy data (Emax) is presented as the mean ± SEM. All data was calculated from at least three independent repeats.
*P < 0.01 compared to HU-308 Emax.
§Enantiomer pair with a lack of statistical significance.
NB = No binding or activity detected at concentrations up to 50 µM.
>10 µM = Displacement of radioactive ligand detected at high concentrations competing ligand but complete displacement curves were not obtained.

Efficacy of Binding to CB2 Receptors.

This assay was performed for selected high potency compounds. $EC_{50}$ values were determined from [$^{35}$S]GTPγS assays by fitting a sigmoidal concentration response curve (Table 2 and FIG. 1A-1G). $E_{max}$ values were calculated as a percentage of the maximal response detected in parallel [$^{35}$S] GTPγS assays with HU-308. As the $E_{max}$ values are determined on a linear scale (not a log of %) these are displayed as the mean±SEM. A Pearson value of 0.9268, indicating good correlation between the data, was generated by plotting the $K_i$ values of compounds against their $EC_{50}$'s determined by GTPγS assay.

TABLE 2

Efficacy of compounds of the invention for the human CB2 receptor

| Compound | HU-Number | $EC_{50}$ (nM) | $E_{max}$ |
|---|---|---|---|
| 14a | HU-909 | 135.5 (45.4, 404) | 76 ± 7%* |
| 14b | HU-910 | 26.4 (10.7, 65.5) | 121 ± 7% |
| 11a | HU-911 | 126.2 (50.7, 315) | 94 ± 4% |
| 16a | HU-913 | 343.6 (151, 785) | 98 ± 3% |
| 23 | HU-926 | 184.9 (72.1, 474) | 51 ± 6%** |
| 25 | HU-928 | 576.8 (291, 1140) | 95 ± 5% |
| | HU-308 | 18.3 (11.6, 28.8) | 100 ± 0% |

Data is shown as mean EC50 values with 95% confidence interval values in parentheses. Mean $E_{max}$ values (± SEM) have been normalised to HU-308 $E_{max}$ response.
n = 5
*P < 0.05,
**P < 0.001.

Figure 1G:
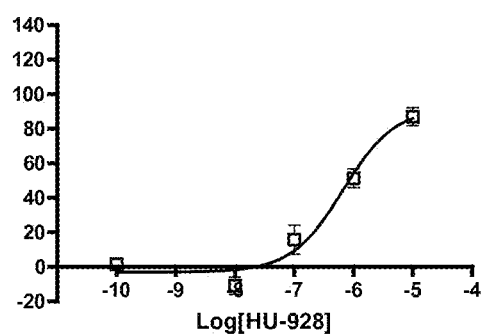

FIGS. 1A-1G show the GTPγS binding graphs for human CB2 receptor of compounds of the invention: HU-308 (FIG. 1A), HU-909 (FIG. 1B), HU-910 (FIG. 1C), HU-911 (FIG. 1D), HU-913 (FIG. 1E), HU-926 (FIG. 1F) and HU-928 (FIG. 1G). Data is shown as [$^{35}$S]GTPγS binding normalised to maximal HU-308 binding under the same experimental conditions.

Example 3

In Vitro Effect of HU-910 on Closed Head Injury

Closed Head Injury Model and Neurobehavioral Evaluation

The study was conducted according to the guidelines of the Institutional Animal Care Committee of the Hebrew University. Male Sabra mice weighing 35 to 50 g were used in all experiments. Animals were kept under controlled light conditions with a 12 h/12 h light/dark cycle. Experimental closed head injury (CHI) was induced using a modified weight drop device developed in our laboratory as described previously (Chen et al., 1996). At 1 h after CHI, the functional status of the mice was evaluated according to a set of 10 neurobehavioral tasks, namely the neurological severity score (NSS). This score is based on the ability of the mice to perform 10 different tasks (Beni-Adani et al., 2001) that evaluate their motor ability, balance, and alertness. One point is given for failing to perform a task. The severity of injury is indicated by the initial NSS, which is evaluated 1 h after CHI and is also a reliable predictor of the later outcome. A score of 10 reflects maximal neurologic impairment, and a decrease of NSS during the recovery period indicates partial recovery of function.

Statistical Analysis

Data was analyzed using the Prism 4.02 programme (GraphPad Software, San Deigo, Calif., USA). The data are expressed as mean±SEM and statistical significance was assessed with one way analysis of variance (ANOVA) followed by a Dunnett's post-hoc analysis for TNF-α levels. Nonparametric NSS values were compared between the two groups at each time point. These data were analyzed for differences between groups at individual times (and not over time within the same group). Hence, Mann-Whitney tests were used for comparisons.

In Vivo Experiment 1:

In this study four groups of mice were subjected to CHI (n=10/group and control n=9), after which the following agents were administered:

Group 1 (Control): Vehicle only (ethanol:cremophor:saline at ratio of 1:1:18), 1 h after CHI.

Group 2: HU-910, 0.1 mg/kg, dissolved in vehicle (1:1:18 ethanol:cremophor:saline), i.p. 1 h after CHI.

Group 3: HU-910, 1.0 mg/kg, dissolved in vehicle (1:1:18 ethanol:cremophor:saline), i.p. 1 h after CHI.

Group 4: HU-910, 10.0 mg/kg, dissolved in vehicle (1:1:18 ethanol:cremophor:saline), i.p. 1 h after CHI.

Figure 2:
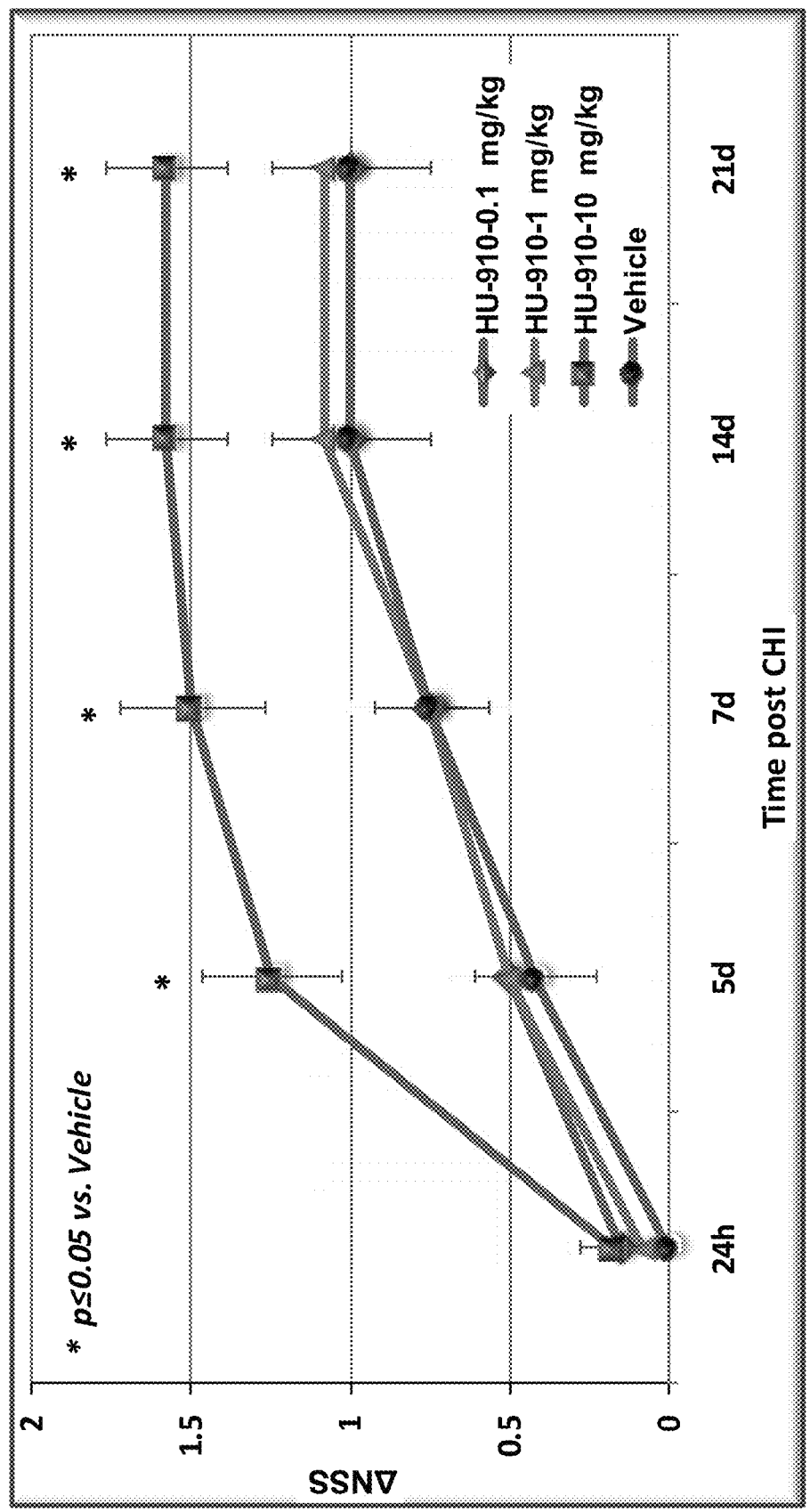
FIG. 2 shows the extent of recovery (measured as ΔNSS (Neurological Severity Score)=NSS(1 h)−NSS(t)) in a period of between 24 h to 21 days post closed head trauma (CHI) for groups receiving different doses of HU-910 (14b), (c1=0.1 mg/kg, c2=1 mg/kg, c3=10 mg/kg, injected i.p. 1 h after CHI). Control group (veh) received the vehicle alone (ethanol:cremophor:saline at ratio of 1:1:18).

The Neurological Severity Score (NSS) was followed during 21 days, and the extent of recovery (measured as ΔNSS=NSS(1 h)−NSS(t)) was calculated and presented in FIG. 2. It is noted that the most effective dose of HU-910 was 10 mg/kg. At days 5 and 7 post injury, the treated mice displayed a significant greater recovery than the controls (vehicle-treated) or lower doses (HU-910 at 0.1 and 1 mg/kg) treated groups.

In Vivo Experiment 2:

In this study four groups of mice were subjected to CHI (n=9/group), after which the following agents were administered:

Group 1 (Control): Vehicle only (ethanol:cremophor:saline at ratio of 1:1:18), 1 h after CHI.

Group 2: HU-910, 10 mg/kg, dissolved in vehicle (1:1:18 ethanol:cremophor:saline), i.p. 1 h after CHI.

Group 3: Specific CB2 antagonist SR144528 (N-[(1S)-endo-1,3,3-trimethylbicyclo[2.2.1]heptan-2-yl]-5-(4-chloro-3-methylphenyl)-1-(4-methylbenzyl)pyrazole-3 carboxamide), (see M. Rinaldi-Carmona, et al. *J. Pharmacol. Exp. Ther.* 284 (1998) 644-650), 1 mg/kg, i.p. 1 h after CHI.

Group 4: Specific CB2 antagonist (SR144528, N-[(1S)-endo-1,3,3-trimethylbicyclo[2.2.1]heptan-2-yl]-5-(4-chloro-3-methylphenyl)-1-(4-methylbenzy)pyrazole-3 carboxamide), 1 mg/kg, i.p. 1 h after CHI and HU-910 10 mg/kg administered 10 min after administration of antagonist.

It is noted that groups 3 and 4 were administered in order to verify that HU-910 indeed acts via the CB2 receptor.

Figure 3:
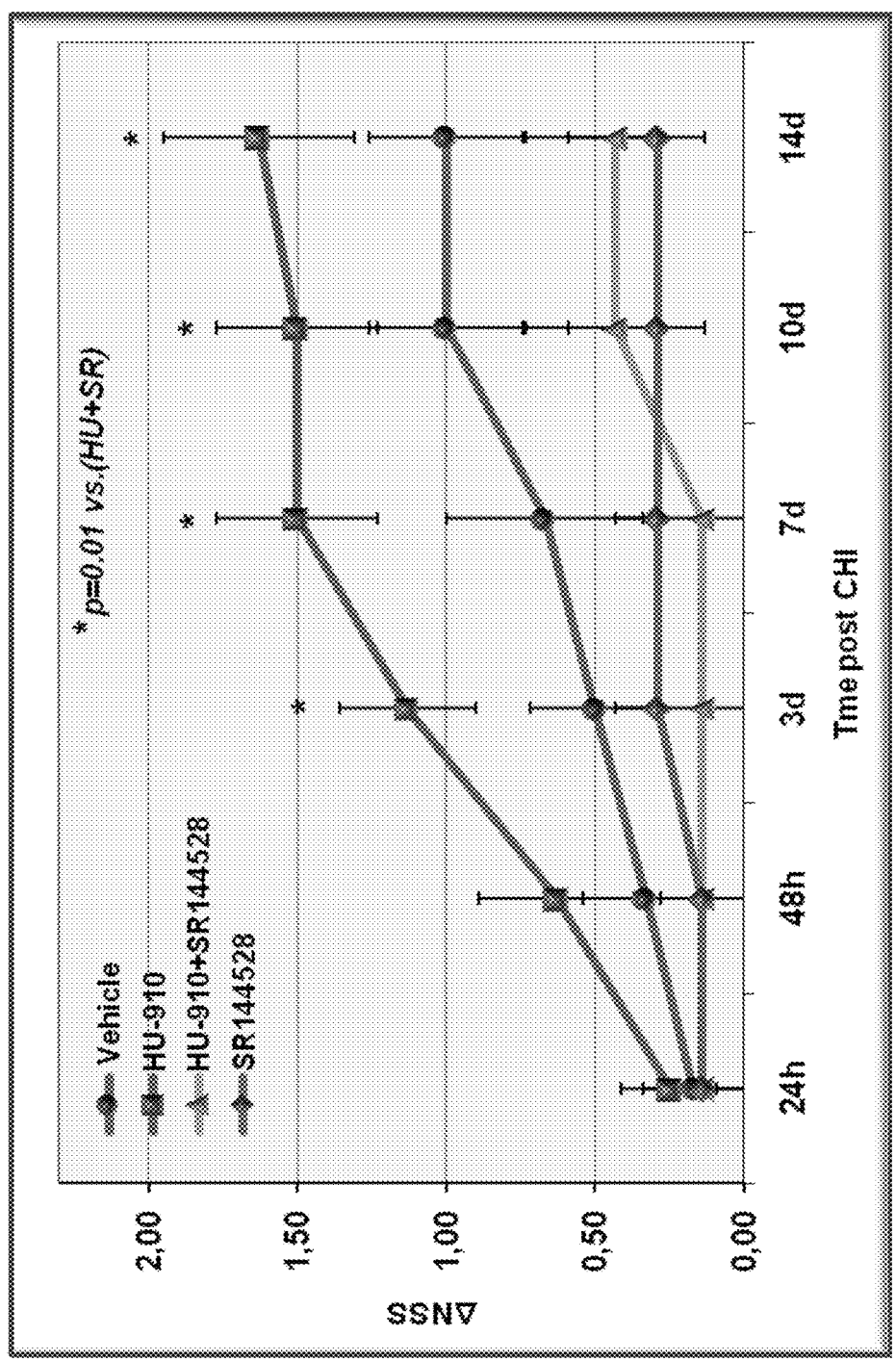
FIG. 3 shows the extent of recovery (measured as ΔNSS (Neurological Severity Score)=NSS(1 h)−NSS(t)) in a period of between 24 h to 14 day post closed head trauma (CHI) for groups receiving: 10 mg/kg of HU-910 (14b) (injected i.p. 1 h after CHI), 1 mg/kg SR144528 CB2 antagonist alone, 1 mg/kg SR144528 CB2 antagonist and 10 mg/kg of HU-910 after 10 min. Control group (veh) received the vehicle alone (ethanol:cremophor:saline at ratio of 1:1:18).

FIG. 3 depicts the extent of recovery of the four groups (measured as ΔNSS=NSS(1 h)−NSS(t)), for a period of 24 h to 14 day post CHI), from which it can be appreciated that in the presence of the antagonist alone (Group 3), the recovery was significantly reduced as compared with the control group (Group 1), administered with the vehicle alone. Moreover, the beneficial effect of HU-910 was reduced to a similar extent in the presence of the antagonist (Group 4). These findings suggest that HU-910 exerts its effect via the CB2 receptor. Thus, it is also stipulated that the endogenous ligands, 2-AG and anandamide that exert their neuro-protective effect by stimulating of the CB2 receptors, provide protection at the post-CHI period, such that when the CB2 receptor is blocked (e.g. with antagonist), their effect is eliminated as well, leading to retarded recovery.

In Vivo Experiment 3:

In this study four groups of mice were subjected to CHI (n=7-8/group), after which the following agents were administered:

Group 1 (Control): Vehicle only (Dimethyl Sulfoxide (DMSO): Tween 80: Saline at ratio of 1:1:18), i.p. 1 h after CHI.

Group 2: HU-910, 10 mg/kg, dissolved in Vehicle, i.p. 1 h after CHI.

Group 3: Specific CB2 antagonist/inverse agonist AM630 (6-Iodo-2-methyl-1-[2-(4-morpholinyl)ethyl]-1H-indol-3-yl](4-methoxyphenyl)methanone) (Ross et al. 1999)), dissolved in Vehicle, 1 mg/kg, i.p. 1 h after CHI and HU-910, dissolved in Vehicle, 10 mg/kg administered 10 min after administration of antagonist/inverse agonist.

Group 4: Specific CB2 antagonist/inverse agonist AM630 (6-Iodo-2-methyl-1-[2-(4-morpholinyl)ethyl]-1H-indol-3-yl](4-methoxyphenyl)methanone), dissolved in Vehicle, 1 mg/kg, i.p. 1 h after CHI It is noted that groups 3 and 4 were administered in order to verify that HU-910 indeed acts via the CB2 receptor.

Figure 4:
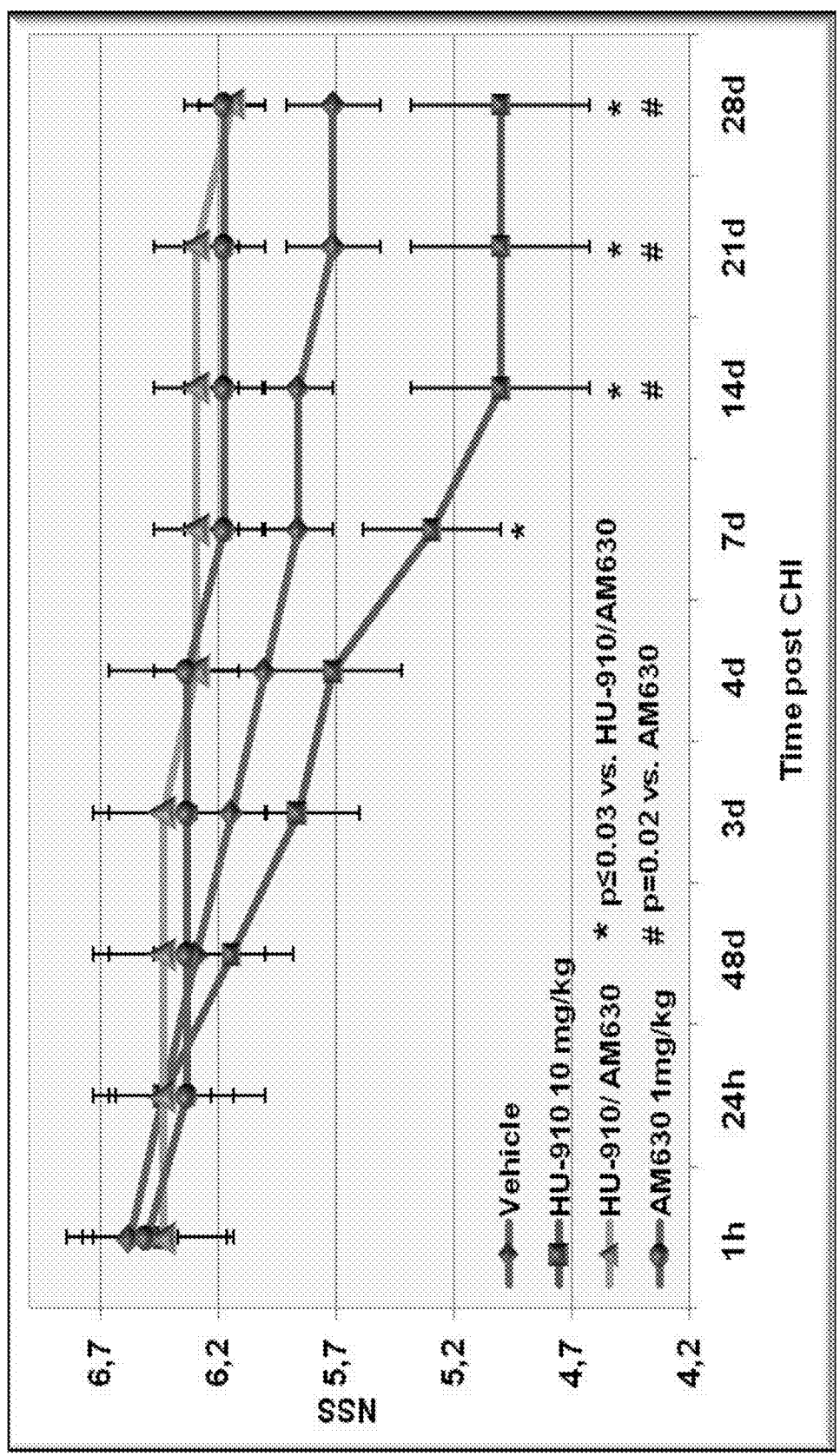
FIG. 4 depicts the recovery of the four groups measured as ΔNSS (measured as ΔNSS (Neurological Severity Score)=NSS(1 h)−NSS(t)), for a period of 1 h to 28 days post CHI.

FIG. 4 depicts the recovery of the four groups measured as ΔNSS, for a period of 1 h to 28 days post CHI, from which it can be appreciated that the beneficial effect of HU-910 (Group 2) was reduced to a similar extent in the presence of the antagonist/inverse agonist (Group 3). These findings suggest that HU-910 exerts its effect via the CB2 receptor.

In Vivo Effect of HU-914 on Closed Head Injury

In Vivo Experiment 4:

In this study four groups of mice were subjected to CHI (n=10/group), after which the following agents were administered:

Group 1 (Control): Vehicle only (ethanol:cremophor:saline at ratio of 1:1:18), 1 h after CHI.

Group 2: HU-914, 5 mg/kg, dissolved in vehicle (1:1:18 ethanol:cremophor:saline), i.p. 1 h after CHI.

Group 3: HU-914, 10 mg/kg, dissolved in vehicle (1:1:18 ethanol:cremophor:saline), i.p. 1 h after CHI.

Group 4: HU-914, 20 mg/kg, dissolved in vehicle (1:1:18 ethanol:cremophor:saline), i.p. 1 h after CHI.

Figure 5:
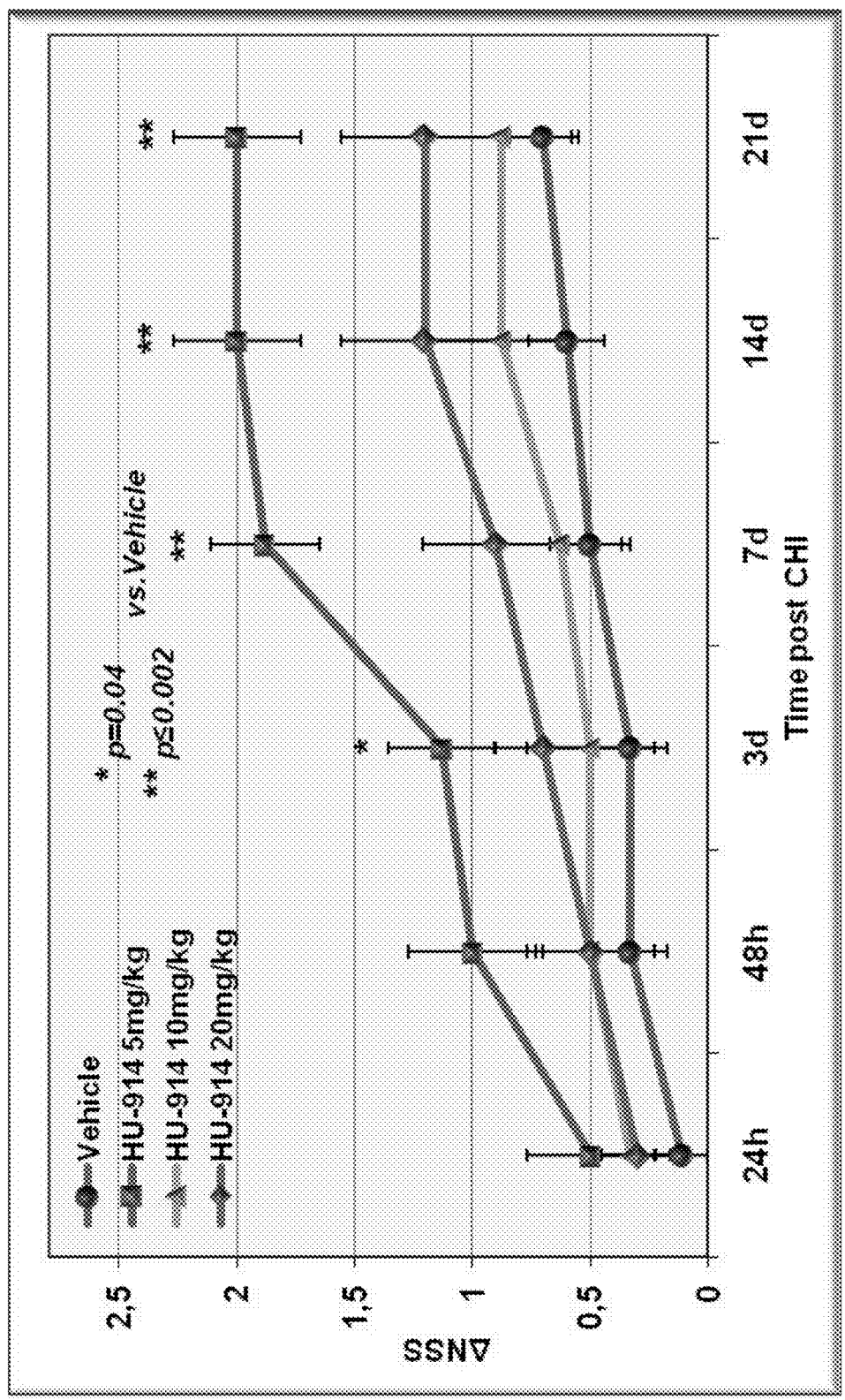
FIG. 5 depicts the Neurological Severity Score (ΔNSS=NSS(1 h)−NSS(t)) was followed during 24 h to 21 days post CHI.

The Neurological Severity Score (ΔNSS) was followed during 21 days and presented in FIG. 5. The most effective dose of HU-914 was 5 mg/kg. Starting at 3 days post injury, the treated mice with HU-914 5 mg/kg displayed a significant greater recovery than the controls (vehicle-treated) or higher doses (HU-914 10 mg/kg and 20 mg/kg) treated group.

In Vivo Experiment 5:

In this study three groups of mice were subjected to CHI (n=10/group), after which the following agents were administered:

Group 1 (Control): Vehicle only (ethanol:cremophor:saline at ratio of 1:1:18), 1 h after CHI.

Group 2: HU-914, 5 mg/kg, dissolved in vehicle (1:1:18 ethanol:cremophor:saline), i.p. 1 h after CHI.

Group 3: Specific CB2 antagonist/inverse agonist (SR144528, N-[(1S)-endo-1,3,3-trimethylbicyclo[2.2.1]heptan-2-yl]-5-(4-chloro-3-methylphenyl)-1-(4-methylbenzyl)pyrazole-3 carboxamide), 1 mg/kg, i.p. 1 h after CHI and HU-914 5 mg/kg administered 10 min after administration of antagonist/inverse agonist.

Figure 6:
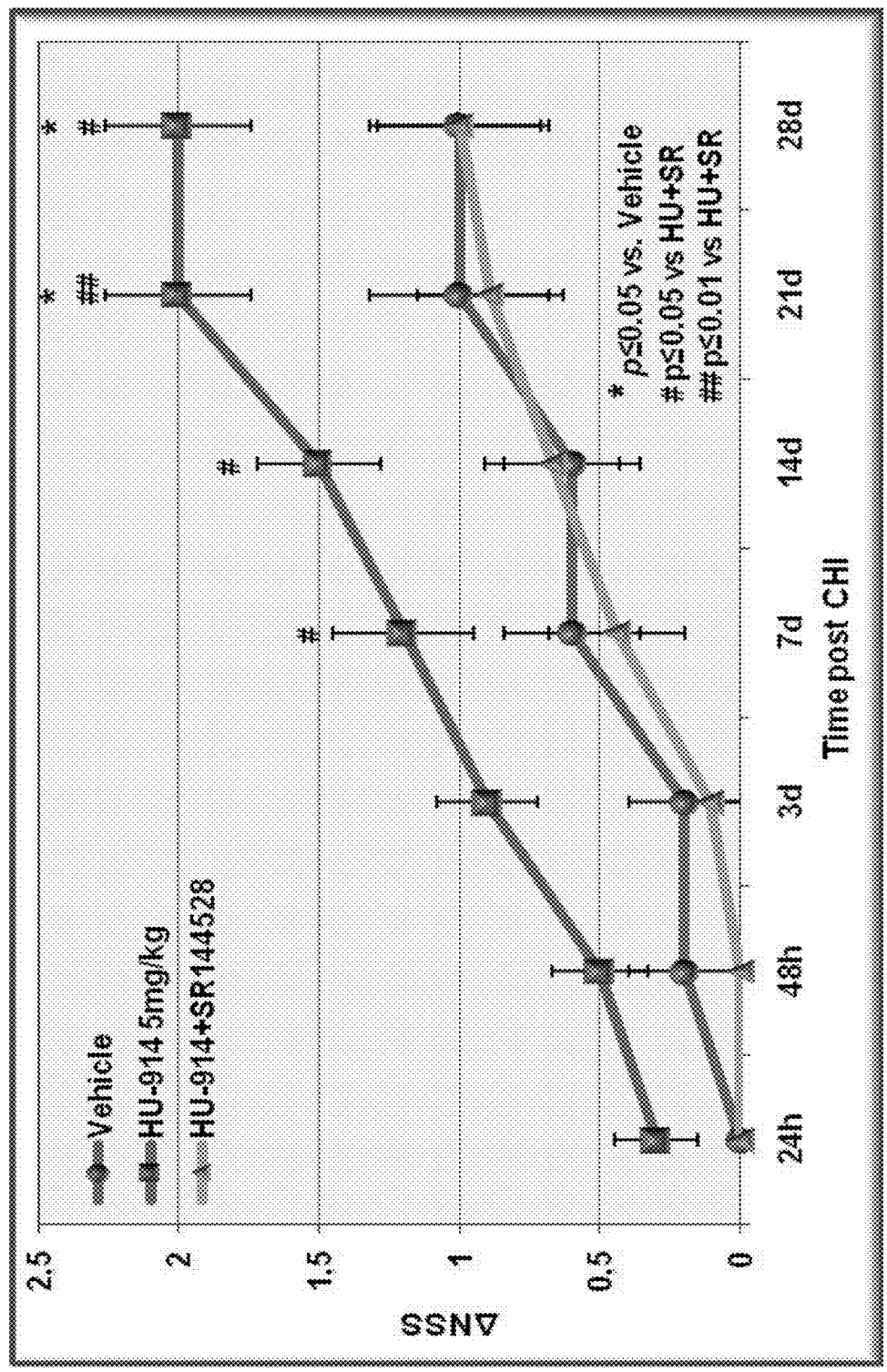
FIG. 6 depicts the extent of recovery of the four groups (measured as ΔNSS=NSS(1 h)−NSS(t), for a period of 24 h to 28 day post CHI).

FIG. 6 depicts the extent of recovery of the four groups (measured as ΔNSS=NSS(1 h)−NSS(t), for a period of 24 h to 28 day post CHI), from which it can be appreciated that in the presence of the antagonist/inverse agonist (Group 3), the recovery achieved by HU-914 (Group 2) was abolished and reduced to a similar extent as in the control group (Group 1), administered with the vehicle alone. These findings suggest that, at least partially, HU-914 exerts its effect via the CB2 receptor.

In Vivo Experiment 6:

In this study four groups of male, C57Bl mice were subjected to CHI (n=7-10/group), after which the following agents were administered:

Group 1 (Control): Vehicle only (ethanol:cremophor:saline at ratio of 1:1:18), i.p. 1 h after CHI.
Group 2: HU-914, 2.5 mg/kg, dissolved in vehicle (1:1:18 ethanol:cremophor:saline), i.p. 1 h after CHI.
Group 3: HU-914, 5 mg/kg, dissolved in vehicle (1:1:18 ethanol:cremophor:saline), i.p. 1 h after CHI.
Group 4: HU-914, 10 mg/kg, dissolved in vehicle (1:1:18 ethanol:cremophor:saline), i.p. 1 h after CHI.

Figure 7:
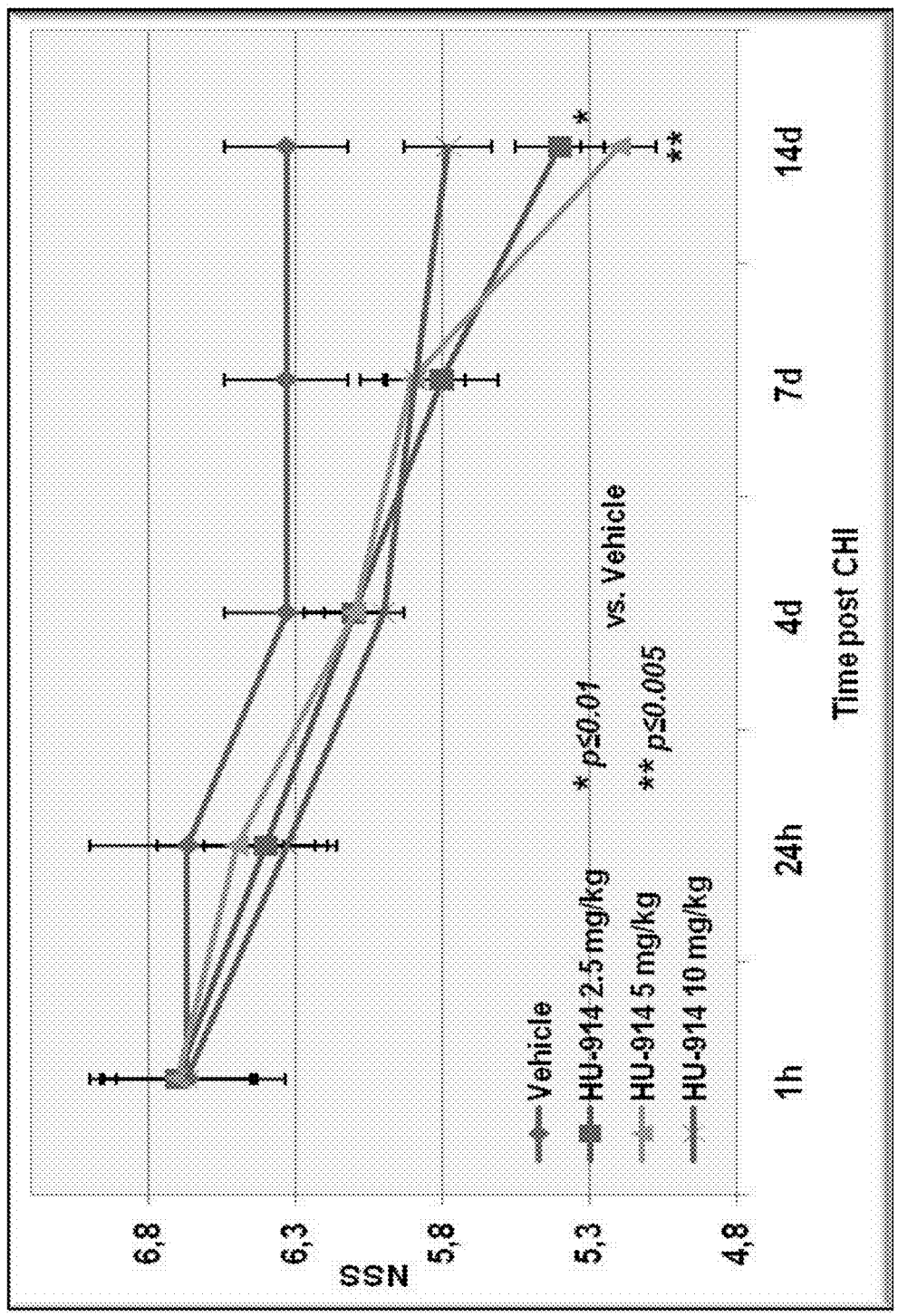
FIG. 7 depicts the Neurological Severity Score (NSS) as followed during 1 h to 14 days post CHI.

The Neurological Severity Score (NSS) was followed during 14 days and presented in FIG. 7. It is noted that the most effective doses of HU-914 in a particular strain of mice were 2.5 mg/kg and 5 mg/kg. At days 14 post injury, the treated mice with HU-914 (2.5 mg/kg and 5 mg/kg) displayed a significant greater recovery than the controls (vehicle-treated) or higher dose (HU-914 at 10 mg/kg) treated group. Similar to Sabra mice, this study represents a dose-response effect of HU-914 in C57Bl mice, in which the lower doses (HU-914 2.5 and 5 mg/kg) were more effective than a higher dose (HU-914 10 mg/kg) or vehicle.

The Effect of HU-914 on TNF-α Production Following CHI.

TNF-α activity can be induced by ischemic and traumatic brain injury starting at 1-2 h and reaching the peak at 4 h following CHI. (Shohami et al., 1997). The next step was to investigate the effect of HU-914 on TNF-α production after CHI. Three groups of mice (n=5-6) were subjected to CHI:

Group 1 (Control): Sham controls received anesthesia and skin incision only.
Group 2: Vehicle only (ethanol:cremophor:saline at ratio of 1:1:18), i.p. 1 h after CHI.
Group 3: HU-914, 5 mg/kg, dissolved in vehicle (1:1:18 ethanol:cremophor:saline), i.p. 1 h after CHI.

Figure 8:
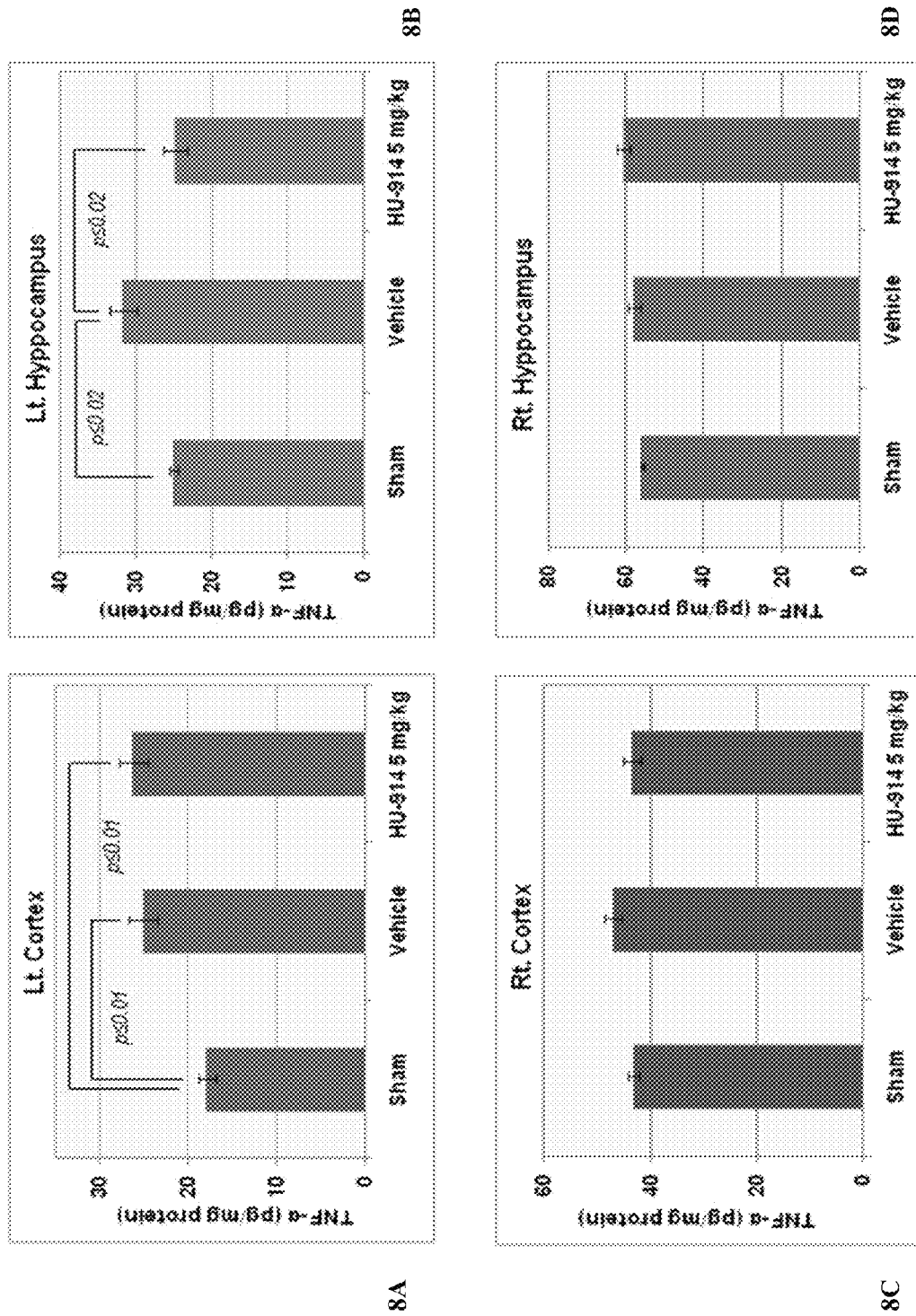
FIGS. 8A-8D depicts TNF-α production following CHI in left Cortex (FIG. 8A), left hippocampus (FIG. 8B), right Cortex (FIG. 8C) and right Hyppocampus (FIG. 8D).

The animals were sacrificed 4 hrs after CHI by decapitation. Brains were rapidly removed and dissected into ipsilateral and contralateral cortical and hippocampal segments that were frozen in liquid nitrogen and kept at −78. The brain tissues were homogenized in ice-cold lysis buffer (50 mM Tris-HCl, 1 mM EDTA, 1 mM EGTA, 0.5 mM $Na_3VO_4$, 0.1% 2-mercaptoethanol, 1% Triton X-100, 50 mM NaF, 5 mM sodium pyrophosphate, 10 mM sodium β-glyceropyrophosphate, 0.1 mM phenylmethanesulfonyl fluoride, and protease inhibitor mixture) (Roche Diagnostics, Indianapolis, Ind.). Following sonication on ice for 45 s and centrifugation at 12,000 rpm for 20 min, protein concentrations in the supernatants were determined using the Bradford method (Bio-Rad Laboratories, Munich, Germany). Supernatants were analyzed by enzyme-linked immunosorbent assay (ELISA) for production of TNF-α, using cytokine specific kit from R&D Systems (Minneapolis, Minn.). HU-914 inhibited TNF-α production in the hippocampus of the injured, left hemisphere, but did not affect the cytokine's level in the left cortex. TNF-α elevation was not detected in the right cortex or hippocampus (FIG. 8).

The invention claimed is:

1. A compound of formula

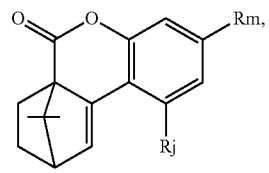

wherein $R_j$ is selected from H, and —$OR_n$ wherein $R_n$ is selected form H, —$COOR_t$, a straight or branched $C_1$-$C_5$ alkyl optionally substituted by at least one group selected from —COOH, —$NH_2$; and $R_t$ is selected from H, $C_1$-$C_5$ alkyl and —$NH_2$; and $R_m$ is selected from a straight or branched $C_6$-$C_{12}$ alkyl, a straight or branched $C_5$-$C_9$ alkoxy; each optionally substituted by at least one group selected from —COOH, —$NH_2$.

2. A compound selected from the group consisting of:

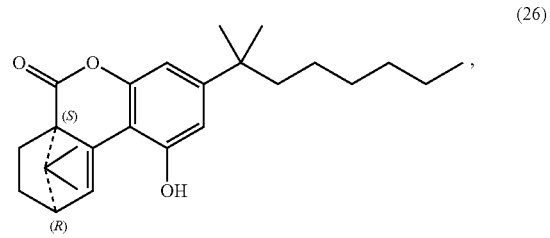

(26)

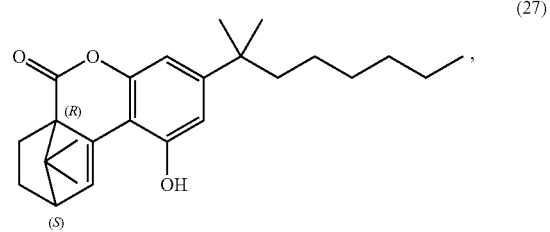

(27)

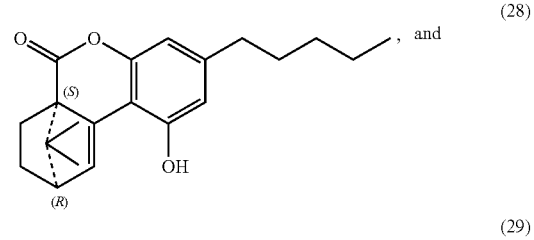

, and (28)

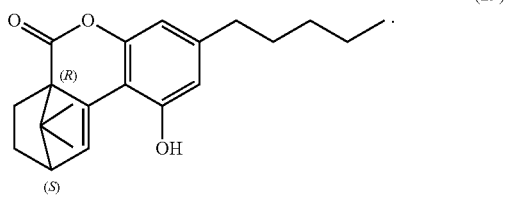

. (29)

3. A pharmaceutical composition comprising a compound according to claim 1.

4. A pharmaceutical composition comprising a compound according to claim 2.

* * * * *